US009783597B2

(12) United States Patent
Torres et al.

(10) Patent No.: US 9,783,597 B2
(45) Date of Patent: Oct. 10, 2017

(54) **METHODS OF TREATING AND PREVENTING *STAPHYLOCOCCUS AUREUS* INFECTIONS AND ASSOCIATED CONDITIONS**

(71) Applicants: Victor J. Torres, New York, NY (US); Francis Alonzo, III, Chicago, IL (US)

(72) Inventors: Victor J. Torres, New York, NY (US); Francis Alonzo, III, Chicago, IL (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/273,914

(22) Filed: Sep. 23, 2016

(65) Prior Publication Data

US 2017/0008953 A1    Jan. 12, 2017

Related U.S. Application Data

(60) Continuation of application No. 14/736,751, filed on Jun. 11, 2015, now Pat. No. 9,481,723, which is a division of application No. 13/527,436, filed on Jun. 19, 2012, now Pat. No. 9,091,689.

(60) Provisional application No. 61/498,596, filed on Jun. 19, 2011.

(51) Int. Cl.
| | |
|---|---|
| *A61K 39/085* | (2006.01) |
| *C07K 16/12* | (2006.01) |
| *A61K 39/40* | (2006.01) |
| *A61K 31/7088* | (2006.01) |
| *A61K 31/724* | (2006.01) |
| *G01N 33/50* | (2006.01) |
| *G01N 33/569* | (2006.01) |
| *A61K 38/16* | (2006.01) |
| *A61K 39/00* | (2006.01) |

(52) U.S. Cl.
CPC ...... *C07K 16/1271* (2013.01); *A61K 31/7088* (2013.01); *A61K 31/724* (2013.01); *A61K 38/164* (2013.01); *A61K 39/085* (2013.01); *A61K 39/40* (2013.01); *C07K 16/12* (2013.01); *G01N 33/5014* (2013.01); *G01N 33/5047* (2013.01); *G01N 33/56938* (2013.01); *A61K 2039/505* (2013.01); *C07K 2317/31* (2013.01); *C07K 2317/76* (2013.01); *G01N 2333/31* (2013.01); *G01N 2469/10* (2013.01); *G01N 2500/10* (2013.01); *G01N 2800/56* (2013.01)

(58) Field of Classification Search
CPC .. A61K 2300/00; A61K 31/351; A61K 31/46; A61K 31/506; A61K 38/164; A61K 2039/505; A61K 31/439; A61K 31/7088; A61K 31/724; A61K 39/085; A61K 39/3955; A61K 39/40; A61K 45/06; C07K 2317/76; C07K 16/12
See application file for complete search history.

(56) References Cited

U.S. PATENT DOCUMENTS

| | | | |
|---|---|---|---|
| 7,608,276 | B2 | 10/2009 | Masignani et al. |
| 7,947,808 | B2 | 5/2011 | Ohishi et al. |
| 2003/0171563 | A1 | 9/2003 | McNamara |
| 2005/0287167 | A1 | 12/2005 | zur Megede et al. |
| 2008/0131457 | A1 | 6/2008 | Taylor et al. |
| 2009/0053235 | A1 | 2/2009 | Taylor et al. |
| 2009/0247570 | A1 | 10/2009 | Mayer |
| 2010/0284909 | A1 | 11/2010 | Wisniewski et al. |
| 2011/0143992 | A1 | 6/2011 | Taub et al. |

FOREIGN PATENT DOCUMENTS

| | | |
|---|---|---|
| EP | 1 593 680 A1 | 11/2005 |
| JP | 2008-513409 A | 5/2008 |
| WO | 02/059148 A2 | 8/2002 |
| WO | 2005/016226 A2 | 2/2005 |
| WO | 2006/032500 A2 | 3/2006 |
| WO | 2007/062150 A2 | 5/2007 |
| WO | 2007/095347 A2 | 8/2007 |
| WO | 2007/144720 A2 | 12/2007 |
| WO | 2007/145689 A1 | 12/2007 |
| WO | 2008/099278 A2 | 8/2008 |
| WO | 2010/119343 A2 | 10/2010 |
| WO | 2011/047011 A2 | 4/2011 |

OTHER PUBLICATIONS

English Translation and Second Office Action for China Patent Application No. 201410532443.5 (mailed Jan. 20, 2017).
English Translation and Fourth Office Action for China Patent Application No. 201280039370.5 (mailed Feb. 13, 2017).
English Translation and Office Action for Japanese Patent Application No. 2014-517100 (Nov. 7, 2016).
English Translation and Office Action for Russian Patent Application No. 2014101488 (Oct. 3, 2016).
English Translation and Second Office Action for China Application No. 201280039369.2 (Oct. 26, 2016).
Verkaik et al., "Immunogenicity of Toxins During *Staphylococcus aureus* Infection," Clin. Infect. Dis. 50:61-68 (2010).
Brown et al., "The Panton-Valentine Leukocidin Vaccine Protects Mice Against Lung and Skin Infections Caused by *Staphylococcus aureus* USA300," Clin. Microbiol. Infect. 15(2):156-164 (2009).
Extended European Search Report for corresponding EP 12801920.5 (8 pages) (Dec. 15, 2014).
Shin et al., "Identification and Characterization of INCB9471, an Allosteric Noncompetitive Small-Molecule Antagonist of C—C Chemokine Receptor 5 with Potent Inhibitory Activity Against Monocyte Migration and HIV-1 Infection," J. Pharmacol. Exp. Ther. 338(1):228-239 (2011).

(Continued)

*Primary Examiner* — Padma V Baskar
(74) *Attorney, Agent, or Firm* — LeClairRyan, a Professional Corporation

(57) ABSTRACT

The present invention relates to methods and compositions for preventing and treating *Staphylococcus aureus* in a subject. Therapeutic compositions of the present invention comprise leukocidin E and/or D proteins or polypeptides and anti-leukocidin E and/or D antibodies. The invention further relates to methods of identifying inhibitors of LukE/D cytotoxicity and inhibitors of LukE/D-leukocyte binding.

14 Claims, 6 Drawing Sheets

(56) References Cited

OTHER PUBLICATIONS

Partial Supplemental European Search Report for EP 12802525.1 (6 pages) (Nov. 19, 2014).
Morinaga et al., "Purification, Cloning and Characterization of Variant LukE-LukD with Strong Leukocidal Activity of Staphylococcal Bi-Component Leukotoxin Family," Microbiol. Immunol. 47(1):81-90 (2003).
Alonzo et al., "*Staphylococcus aureus* Leucocidin ED Contributes to Systemic Infection by Targeting Neutrophils and Promoting Bacterial Growth in Vivo," Molecular Microbiology 83(2):423-435 (2012).
Gravet et al., "Characterization of a Novel Structural Member, LukE-LukD, of the Bi-Component Staphylococcal Leucotoxins Family," FEBS Lett. 436:202-208 (1998).
McNamara et al., "A rot Mutation Restores Parental Virulence to an agr-Null *Staphylococcus aureus* Strain in a Rabbit Model of Endocarditis," Infect. & Immun. 73(6):3806-3809 (2005).
McNamara et al., "Identification, Cloning, and Initial Characterization of rot, a Locus Encoding a Regulator of Virulence Factor Expression in *Staphylococcus aureus*," J. Bacteriol. 182(11):3197-3203 (2000).
International Search Report and Written Opinion for PCT International Patent Application No. PCT/US12/43179 (mailed Dec. 10, 2012).
Ward et al., UniProt Accession No. C8L2Y6, dated Mar. 8, 2011 (retrieved Nov. 20, 2012).
Keppler et al., "Progress Toward a Human CD4/CCR5 Transgenic Rat Model for De Novo Infection by Human Immunodeficiency Virus Type 1," J. Exp. Med. 195(6):719-736 (2002).
International Search Report and Written Opinion for PCT International Patent Application No. PCT/US12/43182 (mailed Dec. 13, 2012).
Vyas et al., "Recurrent Community-Acquired Methicillin-Resistant *Staphylococcus aureus* Infections in an HIV-Infected Person," J. Clin. Microbial. 49(5):2047-2053 (2011).
Kuroda et al., UniProt Accession No. Q99T53, dated Nov. 30, 2010 (retrieved Nov. 29, 2012).
Kuroda et al., UniProt Accession No. QVYA4, dated Nov. 30, 2010 (retrieved Nov. 29, 2012).
Tumang et al., "T Helper Cell-Dependent, Microbial Superantigen-Induced Murine B Cell Activation: Polyclonal and Antigen-Specific Antibody Responses," J. Immunol. 147(2):432-438 (1991).
Lin et al. "New Insights Into the Prevention of Staphylococcal Infections and Toxic Shock Syndrome," Expert Rev. Clin. Pharmacol. 3(6):753-767 (2010).
Ashorn et al., "Elimination of Infectious Human Immunodeficiency Virus from Human T-Cell Cultures by Synergistic Action of CD4-Pseudomonas Exotoxin and Reverse Transcriptase Inhibitors," Proc. Natl. Acad. Sci. USA 87:8889-8893 (1990).
Chavakis et al., "The Anti-Inflammatory Activities of *Staphylococcus aureus*," Trends Immunol. 28(9):408-418 (2007).
Tuen et al., "A Bacterial Leukotoxin for the Prevention of HIV Infection by Selective Killing of CD4 T Cells Targeted by HIV," AIDS Research and Human Retroviruses 26(10):A91 (2010) (abstract).
Extended European Search Report and Search Opinion for EP 12802525.1 (Mar. 26, 2015) (10 pages).
Examination Report for New Zealand Patent Application No. 619942 (Apr. 14, 2015).
Bork et al., "Go Hunting in Sequence Databases but Watch out for the Traps," Trends in Genetics 12:425-427 (1996).
Bork, P., "Powers and Pitfalls in Sequence Analysis: The 70% Hurdle," Genome Research 10:398-400 (2000).
Kolchanov et al., "Single Amino Acid Substitutions Producing Instability of Globular Proteins. Calculation of Their Frequencies in the Entire Mutational Spectra of the alpha- and beta-Subunits of Human Hemoglobin," J. Mol. Evol. 27:154-162 (1988).
Pasquo et al., "Structural Stability of Human Protein Tyrosine Phosphatase ρ Catalytic Domain: Effect of Point Mutations," PLoS ONE 7(2):e32555 (2012).
Brown et al., "Pediatric Antibody Response to Community-acquired *Staphylococcus aureus* Infection is Directed to Panton-Valentine Leukocidin," Clin Vaccine Immunol. 16(1):139-41 (2009).
Gauduchon et al., "Neutralization of *Staphylococcus aureus* Panton Valentine Leukocidin by Intravenous Immunoglobulin In vitro," J Infect Dis. 189(2):346-53 (2004).
Campbell, "Monoclonal Antibody Technology," Chapter 1, published by Elsevier (1984).
Office Action for U.S. Appl. No. 14/468,026 (dated Dec. 3, 2015).
Simon et al., "HIV-1 Dynamics In Vivo: Implications for Therapy," Nature Reviews 1:181-190 (2003).
Zeng et al., "Lymphoid Tissue Structure and HIV-1 Infection: Life or Death for T Cells," Trends in Immunology 33(6):306-314 (2012).
Bownik et al., "In vitro Effects of Staphylococcal Leukocidin LukE/LukD on the Proliferative Ability of Lymphocytes Isolated from Common Carp (*Cyprinus carpio* L.)," Fish & Shellfish Immunol. 20:656-659 (2006).
Second China Office Action for CN 201280039370.5 (Jun. 30, 2015) (translation).
Office Action for Chilean Patent Application No. 3651-2013 (Feb. 2, 2016) (translation).
Office Action for Chilean Patent Application No. 3650-2013 (Feb. 3, 2016) (translation).
Third China Office Action for CN 201280039370.5 (dated Dec. 31, 2015) (translation).
Hiramatsu et al., "Dissemination in Japanese Hospitals of Strains of *Staphylococcus aureus* Heterogeneously Resistant to Vancomycin," Lancet. 350(9092):1670-1673 (1997) (abstract).
GenBank Accession No. BAF78688 submitted Aug. 11, 2012.
China Office Action for CN 201410532443.5 (dated Mar. 8, 2016).
Notice of Reasons for Rejection for JP2014-517100 dated Apr. 25, 2016.
First Examination Report for NZ710439 dated Aug. 26, 2015.
Office Action AU2012273125 dated Jun. 16, 2016.
Examination Report IL229922 dated Jul. 10, 2016 (with English translation).
Office Action CL3650-2013 dated Jul. 19, 2016 (with English translation).
Examination Report EP12801920.5 dated Jul. 7, 2016.
Examination and Search Report for Malaysia Patent Application No. PI 2013004568 (Jan. 13, 2017).
Examination and Search Report for Malaysia Patent Application No. PI 2013004567 (Jan. 13, 2017).
Examination Report for Australian Patent Application No. 2012273123 (Dec. 16, 2016).
European Search Report for European Patent Application 16187708.9 (Jan. 16, 2017).
English Translation and Fifth Office Action for China Patent Application No. 201280039370.5 (Jul. 20, 2017).

METHODS OF TREATING AND PREVENTING *STAPHYLOCOCCUS AUREUS* INFECTIONS AND ASSOCIATED CONDITIONS

This application is a continuation of U.S. patent application Ser. No. 14/736,751, filed Jun. 11, 2015, now U.S. Pat. No. 9,481,723, which is a division of U.S. patent application Ser. No. 13/527,436, filed June 19, 201.2, now U.S. Pat. No. 9,091,689, issued on Jul. 28, 2015, which claims the benefit of U.S. Provisional Patent Application Ser. No. 61/498,596, filed Jun. 19, 2011, each of which is hereby incorporated by reference in its entirety.

FIELD OF THE INVENTION

This invention relates to methods of screening for, treating, and preventing *Staphylococcus aureus* infections and *Staphylococcus aureus* associated conditions.

BACKGROUND OF THE INVENTION

*Staphylococcus aureus* ("*S. aureus*") is a bacterium that commensally colonizes more than 25% of the human population. Importantly, this organism is capable of breaching its initial site of colonization, resulting in bacterial dissemination and disease. *S. aureus* is the leading cause of nosocomial infections, is the most common etiological agent of infectious endocarditis as well as skin and soft tissue infections, and is one of the four leading causes of food-borne illness. Altogether, *S. aureus* infects more than 1.2 million patients per year in U.S. hospitals. The threat of *S. aureus* to human health is further highlighted by the emergence of antibiotic-resistant strains (i.e., methicillin-resistant *S. aureus* (MRSA) strains), including strains that are resistant to vancomycin, an antibiotic considered the last line of defense against *S. aureus* infection. These facts highlight the importance of developing novel therapeutics against this important pathogen.

*S. aureus* produces a diverse array of virulence factors and toxins that enable this bacterium to neutralize and withstand attack by different kinds of immune cells, specifically subpopulations of white blood cells that make up the body's primary defense system. The production of these virulence factors and toxins allow *S. aureus* to maintain an infectious state (see Nizet, "Understanding How Leading Bacterial Pathogens Subvert Innate Immunity to Reveal Novel Therapeutic Targets," *J. Allergy Clin. Immunol.* 120(1):13-22 (2007)). Among these virulence factors, *S. aureus* produces several bi-component leukotoxins, which damage membranes of host defense cells and erythrocytes by the synergistic action of two non-associated proteins or subunits (see Menestrina et al., "Mode of Action of Beta-Barrel Pore-Forming Toxins of the Staphylococcal Alpha-Hemolysin Family," *Toxicol.* 39(11):1661-1672 (2001)). Among these bi-component leukotoxins, gamma-hemolysin (HlgAB and HlgCB) and the Pantone-Valentine Leukocidin (PVL) are the best characterized.

The toxicity of the leukocidins towards mammalian cells involves the action of two components or subunits. The first subunit is named class S-subunit (i.e., "slow-eluted"), and the second subunit is named class F-subunit (i.e., "fast-eluted"). The S- and F-subunits act synergistically to form pores on white blood cells including monocytes, macrophages, dendritic cells, and neutrophils (collectively known as phagocytes) (see Menestrina et al., "Mode of Action of Beta-Barrel Pore-Forming Toxins of the Staphylococcal Alpha-Hemolysin Family," *Toxicol.* 39(11):1661-1672 (2001)). The mechanism by which the bi-component toxins form pores in target cell membranes is not entirely understood. The proposed mechanism of action of these toxins involves binding of the S-subunit to the target cell membrane, most likely through a receptor, followed by binding of the F-subunit to the S-subunit, thereby forming an oligomer which in turn forms a pre-pore that inserts into the target cell membrane (Jayasinghe et al., "The Leukocidin Pore: Evidence for an Octamer With Four LukF Subunits and Four LukS Subunits Alternating Around a Central Axis," *Protein. Sci.* 14(10):2550-2561 (2005)). The pores formed by the bi-component leukotoxins are typically cation-selective. Pore formation causes cell death via lysis, which in the cases of the target white blood cells, has been reported to result from an osmotic imbalance due to the influx of cations (Miles et al., "The Staphylococcal Leukocidin Bicomponent Toxin Forms Large Ionic Channels," *Biochemistry* 40(29):8514-8522 (2001)).

In addition to PVL (also known as leukocidin S/F-PV or LukSF-PV) and gamma-hemolysin (HlgAB and HlgCB), the repertoire of bi-component leukotoxins produced by *S. aureus* is known to include leukocidin E/D ("LukE/D"), leukocidin A/B ("LukAB") and leukocidin M/F ("LukMF"). Thus, the S-class subunits of these bi-component leukocidins include HlgA, HlgC, LukE, LukS-PV, LukA, and LukM, and the F-class subunits include HlgB, LukD, LukF-PV, LukB, and LukF'-PV, The *S. aureus* S- and F-subunits are not leukocidin-specific. That is, they are interchangeable such that other bi-component combinations could make a functional pore in a white blood cell, greatly increasing the repertoire of leukotoxins (Meyer et al., "Analysis of the Specificity of Panton-Valentine Leucocidin and Gamma-Hemolysin F Component Binding," *Infect. Immun.* 77(1): 266-273 (2009)).

Designing effective therapy to treat MRSA infection has been especially challenging. In addition to the resistance to methicillin and related antibiotics, MRSA has also been found to have significant levels of resistance to macrolides (e.g., erythromycin), beta-lactamase inhibitor combinations (e.g., Unasyn, Augmentin), and fluoroquinolones (e.g. ciprofloxacin), as well as to clindamycin, trimethoprim/sulfamethoxisol (Bactrim), and rifampin. In the case of serious *S. aureus* infection, clinicians have resorted to intravenous vancomycin. However, there have been reports of *S. aureus* resistance to vancomycin. Thus, there is a need to develop new treatments that effectively combat *S. aureus* infection.

The present invention is directed to overcoming these and other limitations in the art.

SUMMARY OF THE INVENTION

A first aspect of the present invention relates to a composition comprising a therapeutically effective amount of an isolated a Leukocidin E (LukE) protein or polypeptide thereof, an isolated Leukocidin D (LukD) protein or polypeptide thereof, or a combination thereof, and a pharmaceutically acceptable carrier.

Another aspect of the present invention relates to a method of immunizing against a *Staphylococcus aureus* infection in a subject. This method involves administering a composition of the present invention in an amount effective to immunize against *S. aureus* infection in the subject.

Another aspect of the present invention relates to a composition comprising a therapeutically effective amount of an antibody selected from the group consisting of a LukE antibody, a LukD antibody, or a combination thereof, and a pharmaceutically acceptable carrier.

Another aspect of the present invention is directed to a method of preventing a *S. aureus* infection and/or *S. aureus*-associated conditions in a subject. This method involves administering a composition comprising an antibody selected from the group consisting of a LukE antibody, a LukD antibody, or a combination thereof, in an amount effective to prevent *S. aureus* infection and/or *S. aureus* associated condition in the subject.

A further aspect of the present invention is directed to a method of treating a *S. aureus* infection and/or *S. aureus*-associated conditions in a subject. This method involves administering a composition comprising one or more inhibitors of LukE/D mediated cytotoxicity in an amount effective to treat the *S. aureus* infection and/or the *S. aureus* associated condition in the subject.

A further aspect of the present invention relates to a method of predicting severity of an *S. aureus* infection. This method involves culturing *S. aureus* obtained from an infected subject via a fluid or tissue sample from the subject and quantifying LukE and/or LukD expression in the cultured *S. aureus*. The quantified amounts of LukE and/or LukD in the sample from the subject are compared to the amount of LukE and/or LukD in a control sample which produces little or undetectable amounts of LukE and/or LukD and the severity of the *S. aureus* infection is predicted based on said comparing.

Another aspect of the present invention relates to a method of treating a subject with a *S. aureus* infection. This method involves culturing *S. aureus* obtained from an infected subject via a fluid or tissue sample from the subject and quantifying LukE and/or LukD expression in the cultured *S. aureus*. The quantified amounts of LukE and/or LukD in the sample from the subject are compared to the amount of LukE and/or LukD in a control sample which produces little or undetectable amounts of LukE and/or LukD and a suitable treatment for the subject is determined based on this comparison. The method further involves administering the determined suitable treatment to the subject to treat the *S. aureus* infection.

Another aspect of the present invention relates to a method of identifying inhibitors of LukE/D cytotoxicity. This method involves providing a cell population, a preparation containing LukE/D, and a candidate LukE/D inhibitor. The cell population is exposed to the preparation containing LukE/D in the presence and absence of the candidate inhibitor, and LukE/D mediated cytotoxicity is measured in the presence and in the absence of the candidate inhibitor. The measured amount of cytotoxicity in the presence and in the absence of the candidate inhibitor is compared and an inhibitor of LukE/D cytotoxicity is identified based on that comparison.

Another aspect of the present invention relates to a method of identifying inhibitors of LukE/D mediated pore formation. This method involves providing a population of leukocytes, a preparation containing LukE and LukD, and a candidate inhibitor. The leukocyte population is exposed to the preparation containing LukE and LukD in the presence and absence of the candidate inhibitor, and pore formation on the leukocyte population is measured in the presence and absence of the candidate inhibitor. The measured amount of pore formation in the presence and in the absence of the candidate inhibitor is compared, and an inhibitor of LukE/D mediated pore formation is identified based on that comparison.

Another aspect of the present invention is directed to a method of identifying inhibitors of LukE and/or LukD leukocyte binding. This method involves providing a population of leukocytes, a preparation containing a detectably labeled LukE and LukD, and a candidate inhibitor. The cell population is exposed to the preparation containing the detectably labeled LukE and LukD in the presence and absence of the candidate inhibitor, and labeled LukE and/or LukD binding to the leukocyte population is measured in the presence and absence of the candidate inhibitor. The measured amount of LukE and/or LukD leukocyte binding in the presence and in the absence of the candidate inhibitor is compared and an inhibitor of LukE and/or LukD leukocyte binding is identified based on that comparison.

The tremendous success of *S. aureus* as a pathogen is in part due to its ability to express an arsenal of factors that harm the host. Among these factors are a number of bacterial protein toxins that are secreted into the extracellular milieu where they act by killing host cells. Leukocidin E/D (LukE/D) is a poorly characterized toxin produced by *S. aureus*. As demonstrated herein, this toxin targets and kills host leukocytes, which are key immune cells involved in protecting the host from *S. aureus* infection. The finding that LukE/D is critical to pathogenesis in vivo, highlights the importance of this toxin in the disease process. As described herein, immunization with LukE and/or LukD generates neutralizing antibodies against *S. aureus*. Therefore, active and/or passive vaccine strategies offer a novel therapeutic strategy to prevent *S. aureus* infection. In addition, direct inhibition of LukE/D meditated cytotoxicity offers a novel means of treating individuals with *S. aureus* infection.

BRIEF DESCRIPTION OF THE DRAWINGS

FIG. 1A is a survival curve showing that an Δagr Δrot double mutant exhibits WT virulence characteristics in mice. Survival of mice was monitored after intravenous injection with ~1×10$^7$ CFU of *S. aureus* WT, Δagr, or Δagr Δrot double mutants. Total number of mice per group were N=6. Statistical significance between curves was determined using the Log-rank (Mantel-Cox) test. ***, p≤0.0005. In FIG. 1B, the production of leukotoxins is restored in an Δagr Δrot double mutant. Shown are immunoblots of protein samples from TCA precipitated bacterial culture supernatants (grown for 5 hours in RPMI+CAS) of the following strains: WT, Δagr, and Δagr Δrot. Negative control lanes contain TCA precipitated supernatant from respective leukotoxin deletion mutants (ΔlukE/D, ΔlukA/B, Δhla, ΔhlgC). ΔlukE/D ΔhlgACB double mutant exoproteins were also probed in all the LukE immunoblots as a control for LukE antibody cross-reactivity.

As shown in FIG. 3A, optimal lukE/D gene expression is dependent on derepression of Rot. Transcriptional fusions of the lukE/D promoter region to GFP were used to measure activation of the promoter in broth culture in the following strain backgrounds (WT, Δagr, Δrot, and Δagr Δrot). GFP fluorescence was measured over time and values expressed as relative fluorescence units (RFU) after normalization to bacterial Optical Density at 600 nm. Values shown are results of three experiments performed in triplicate. In FIG. 3B, Rot binds to the lukE/D promoter. FIG. 3B is an immunoblot of a promoter pull-down of either biotinylated intragenic DNA (non-specific) or lukE/D promoter DNA bound to M280 streptavidin magnetic beads and incubated with S. aureus whole cell lysates. Rot was detected via immunoblot using an anti-Rot antibody.

FIGS. 4A and 4B show verification of the lukE/D deletion in S. aureus Newman. In FIG. 4A, PCR of S. aureus genomic DNA with lukE specific primers is shown. Shown in FIG. 4B are immunoblots of protein samples from TCA precipitated bacterial culture supernatants (grown for 5 hours in RPMI+CAS) of the following strains: WT, ΔlukE/D, ΔlukE/D::plukE/D, ΔhlgACB, and ΔhlgACB. ΔlukE/D mutant exoproteins were also probed as a control for LukE antibody cross-reactivity. FIGS. 4C-4F show that ΔlukE/D mutant is severely compromised for virulence in mice. In FIGS. 4C and 4D, the survival of mice was monitored after intravenous injection with ~1×10$^7$ CFU (FIG. 4C) or ~1×10$^8$ CFU (FIG. 4D) of S. aureus WT, ΔlukE/D, and ΔlukE/D::plukE/D strains. Total number of mice per group were N=6. Statistical significance between survival curves was determined using the Log-rank (Mantel-Cox) test. , p≤0.005; *, p≤0.0005. FIGS. 4E and 4F depict enumeration of bacterial CFU (FIG. 4E) and gross pathology (FIG. 4F) from kidneys 96 hours post-infection with ~1×10$^7$ CFU of the same strains described for FIGS. 4C and 4D. Arrows designate locations of kidney abscesses. Statistical significance was determined using 1-Way ANOVA with Tukey's multiple comparisons posttest. , p≤0.005; *, p≤0.0005.

FIG. 5A is a cell viability curve showing that purified recombinant LukE/D is toxic to the human monocyte-like cell line THP-1. The THP-1 cell line was intoxicated with recombinant LukE, LukD, or a mixture of LukE+LukD (LukE/D). Cell viability was monitored 1 hour post-intoxication using CellTiter, where cells treated with medium were set at 100% viable. Results represent the average of triplicate samples±S.D. Purified recombinant LukE/D is not toxic to the human HL60 cell line, as shown in the cell viability curve of FIG. 5B. The HL60 cell line was intoxicated as above and cell viability was monitored 1 hour post-intoxication using CellTiter, where cells treated with medium were set at 100% viable. In contrast, the cell viability curves of FIG. 5C show purified recombinant LukE/D is toxic to both primary human (left graph) and primary murine (right graph) neutrophils (also known as polymorphonuclear neutrophils or PMNs). The PMNs were intoxicated as above and cell viability was monitored 1 hour post-intoxication using CellTiter, where cells treated with medium were set at 100% viable. LukE/D mediates cytotoxicity toward host cells THP-1 cells by forming pores in the cell membrane as shown in FIG. 5D. THP-1 and HL60 cells were incubated with purified LukE/D, and pore formation was measured with an ethidium bromide incorporation assay. Mean fluorescence of triplicate experiments are shown for both THP-1 and HL60. FIG. 5E shows a fluorescence microscopy image of ethidium bromide uptake of LukE/D treated (30 µg/ml) and control (no toxin) THP-1 cells.

DETAILED DESCRIPTION OF THE INVENTION

Figures 1A, 1B:
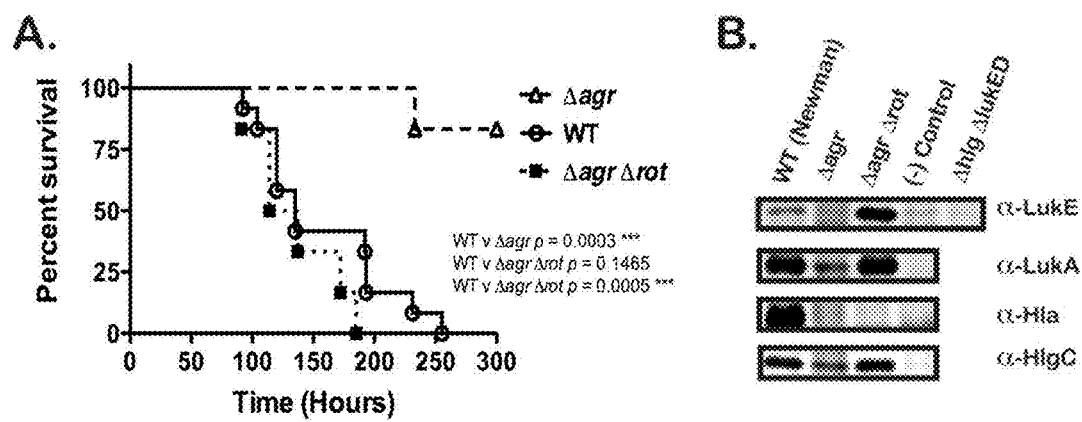
FIGS. 1A-1B show that deletion of the rot gene in an *S. aureus* lacking the agr locus (Δagr Δrot) restores virulence in mice to wild type ("WT") levels and leads to overproduction of LukE/D.

A first aspect of the present invention relates to a composition comprising a therapeutically effective amount of an isolated LukE protein or polypeptide thereof, an isolated LukD protein or polypeptide thereof, or a combination thereof, and a pharmaceutically acceptable carrier.

In one embodiment of the invention, the composition comprises an isolated LukE protein or polypeptide. In another embodiment of the invention, the composition comprises an isolated LukD protein or polypeptide. In yet another embodiment of the invention the composition comprises both LukE and LukD proteins or polypeptides.

In accordance with this aspect of the invention, suitable isolated LukE proteins include those derived from any strain of S. aureus. The amino acid sequence of LukE proteins from various strains of S. aureus that are suitable for the composition of the present invention are shown in the Table 1 below (i.e., SEQ ID Nos:1-10). SEQ ID NO:11 of Table 1 is a LukE consensus sequence demonstrating the high level of sequence identity across LukE proteins of various S. aureus strains. Accordingly, in one embodiment of the present invention, the isolated LukE protein comprises an amino acid sequence of SEQ ID NO:11. In another embodiment of the present invention, the isolated LukE protein comprises an amino acid sequence having about 70-80% sequence similarity to SEQ ID NO:11, more preferably, about 80-90% sequence similarity to SEQ ID NO:11, and more preferably 90-95% sequence similarity to SEQ ID NO:11, and most preferably about 95-99% sequence similarity to SEQ ID NO:11.

In another embodiment of the present invention, the composition comprises an isolated immunogenic polypeptide of LukE. Suitable LukE polypeptides are about 50 to about 100 amino acids in length. More preferably LukE polypeptides are between about 100-200 amino acids in length, more preferably between about 200-250 amino acids in length, and most preferably between 250-300 amino acids in length. The N-terminal amino acid residues of the full-length LukE represent the native secretion/signal sequence. Thus, the "mature" secreted form of LukE is represented by amino acid residues 29-311 in each of SEQ ID NOs:1-10 and SEQ ID NO:11. Correspondingly, amino acid residues 1-311 in each of SEQ ID NOs:1-10 and SEQ ID NO:11 are referred to as the "immature" form of LukE. Accordingly, in one embodiment of the present invention, the LukE polypeptide comprises amino acid residues 29-311 of SEQ ID NO:11. Alternatively, the LukE polypeptide of the present invention comprises amino acid residues 48-291, amino acids 29-301, or amino acids 48-301 of SEQ ID NO:11. These LukE polypeptides lack LukE activity but maintain antigenicity. In either case, suitable LukE polypeptides also include those polypeptides comprising an amino acid sequence having about 70-80% sequence similarity, preferably 80-90% sequence similarity, more preferably 90-95% sequence similarity, and most preferably 95-99% sequence similarity to amino acid residues 29-311 of SEQ ID NO:11, amino acid residues 48-291 of SEQ ID NO:11, amino acid residues 29-301 of SEQ ID NO:11, or amino acid residues 48-301 of SEQ ID NO:11.

In accordance with this aspect of the invention, suitable isolated LukD proteins include those proteins derived from any strain of S. aureus. The amino acid sequence of LukD proteins from various strains of S. aureus that are suitable for the composition of the present invention are shown in the Table 2 below (i.e., SEQ ID Nos: 12-21). SEQ ID NO:22 of Table 2 is a LukD consensus sequence demonstrating the high level of sequence identity across LukD proteins of various S. aureus strains. Accordingly, in one embodiment of the present invention, the isolated LukD protein comprises an amino acid sequence of SEQ ID NO:22. In another embodiment of the present invention, the isolated LukD protein comprises an amino acid sequence having about 70-80% sequence similarity to SEQ ID NO:22, preferably, about 80-90% sequence similarity to SEQ ID NO:22, and more preferably 90-95% sequence similarity to SEQ ID NO:22, and most preferably about 95-99% sequence similarity to SEQ ID NO:22.

In another embodiment of the present invention, the composition comprises an isolated immunogenic polypeptide of LukD. Suitable LukD polypeptides are about 50 to about 100 amino acids in length. More preferably LukD polypeptides are between about 100-200 amino acids in length, more preferably between about 200-250 amino acids in length, and most preferably between 250-300 amino acids in length. The N-terminal amino acid residues of the full-length LukD represent the native secretion/signal sequence. Thus, the mature secreted form of LukD is represented by amino acid residues 27-327 in each of SEQ ID NOs:12-21 and SEQ ID NO:22. Correspondingly, amino acid residues 1-327 of SEQ ID NOs:12-21 and SEQ ID NO:22 are referred to as the "immature" form of LukD. Accordingly, in one embodiment of the present invention, the LukE polypeptide comprises amino acid residues 27-327 of SEQ ID NO:22. Alternatively, the LukE polypeptide of the present invention comprises amino acid residues 46-307, 27-312, and 46-312 of SEQ ID NO:22. These LukD polypeptide lack LukD activity but maintain antigenicity. In either case, suitable polypeptides also include those polypeptide comprising an amino acid sequence having about 70-80% sequence similarity, preferably 80-90% sequence similarity, more preferably 90-95% sequence similarity, and most preferably 95-99% sequence similarity to amino acid residues 27-327 of SEQ ID NO:22, amino acid residues 46-307 of SEQ ID NO:22, amino acid residues 27-312 of SEQ ID NO:22, or amino acid residues 46-312 of SEQ ID NO:22.

TABLE 1

S. Aureus LukE Sequence Alignment

| S. Aureus Strain | | | |
|---|---|---|---|
| Newman | MFKKKMLAATLSVGLIAPLASPIQESRANTNIENIGDGAEVIKRTEDVSS | 50 | SEQ ID NO: 1 |
| MW2 | MFKKKMLAATLSVGLIAPLASPIQESRANTNIENIGDGAEVIKRTEDVSS | 50 | SEQ ID NO: 2 |
| USA_300_FPR3757 | MFKKKMLAATLSVGLIAPLASPIQESRANTNIENIGDGAEVIKRTEDVSS | 50 | SEQ ID NO: 3 |
| COL | MFKKKMLAATLSVGLIAPLASPIQESRANTNIENIGDGAEVIKRTEDVSS | 50 | SEQ ID NO: 4 |
| USA_300_TCH1516 | MFKKKMLAATLSVGLIAPLASPIQESRANTNIENIGDGAEVIKRTEDVSS | 50 | SEQ ID NO: 5 |
| N315 | MFKKKMLAATLSVGLIAPLASPIQESRANTNIENIGDGAEVIKRTEDVSS | 50 | SEQ ID NO: 6 |
| D30 | MFKKKMLAATLSVGLIAPLASPIQESRANTNIENIGDGAEVIKRTEDVSS | 50 | SEQ ID NO: 7 |
| Mu50 | MFKKKMLAATLSVGLIAPLASPIQESRANTNIENIGDGAEVIKRTEDVSS | 50 | SEQ ID NO: 8 |
| TCH_70 | MFKKKMLAATLSVGLIAPLASPIQESRANTNIENIGDGAEVIKRTEDVSS | 50 | SEQ ID NO: 9 |
| MRSA131 | MFKKKMLAATLSVGLIAPLASPIQESRANTNIENIGDGAEVIKRTEDVSS | 50 | SEQ ID NO: 10 |
| | ************************************************** | | |
| LukE Consensus Sequence | MFKKKMLAATLSVGLIAPLASPIQESRANTNIENIGDGAEVIKRTEDVSS | 50 | SEQ ID NO: 11 |
| Newman | KKWGVTQNVQFDFVKDKKYNKDALIVKMQGFINSRTSFSDVKGSGYELTK | 100 | |
| MW2 | KKWGVTQNVQFDFVKDKKYNKDALIVKMQGFINSRTSFSDVKGSGYELTK | 100 | |
| USA_300_FPR3757 | KKWGVTQNVQFDFVKDKKYNKDALIVKMQGFINSRTSFSDVKGSGYELTK | 100 | |
| COL | KKWGVTQNVQFDFVKDKKYNKDALIVKMQGFINSRTSFSDVKGSGYELTK | 100 | |
| USA_300_TCH1516 | KKWGVTQNVQFDFVKDKKYNKDALIVKMQGFINSRTSFSDVKGSGYELTK | 100 | |
| N315 | KKWGVTQNVQFDFVKDKKYNKDALIVKMQGFINSRTSFSDVKGSGYELTK | 100 | |
| D30 | KKWGVTQNVQFDFVKDKKYNKDALIVKMQGFINSRTSFSDVKGSGYELTK | 100 | |
| Mu50 | KKWGVTQNVQFDFVKDKKYNKDALIVKMQGFINSRTSFSDVKGSGYELTK | 100 | |
| TCH_70 | KKWGVTQNVQFDFVKDKKYNKDALIVKMQGFINSRTSFSDVKGSGYELTK | 100 | |
| MRSA131 | KKWGVTQNVQFDFVKDKKYNKDALIVKMQGFINSRTSFSDVKGSGYELTK | 100 | |
| | ************************************************** | | |
| LukE Consensus Sequence | KKWGVTQNVQFDFVKDKKYNKDALIVKMQGFINSRTSFSDVKGSGYELTK | | |
| Newman | RMIWPFQYNIGLTTKDPNVSLINYLPKNKIETTDVGQTLGYNIGGNFQSA | 150 | |
| MW2 | RMIWPFQYNIGLTTKDPNVSLINYLPKNKIETTDVGQTLGYNIGGNFQSA | 150 | |
| USA_300_FPR3757 | RMIWPFQYNIGLTTKDPNVSLINYLPKNKIETTDVGQTLGYNIGGNFQSA | 150 | |
| COL | RMIWPFQYNIGLTTKDPNVSLINYLPKNKIETTDVGQTLGYNIGGNFQSA | 150 | |

TABLE 1 -continued

S. Aureus LukE Sequence Alignment

| | | |
|---|---|---|
| USA_300_TCH1516 | RMIWPFQYNIGLTTKDPNVSLINYLPKNKIETTDVGQTLGYNIGGNFQSA | 150 |
| N315 | RMIWPFQYNIGLTTKDPNVSLINYLPKNKIETTDVGQTLGYNIGGNFQSA | 150 |
| D30 | RMIWPFQYNIGLTTKDPNVSLINYLPKNKIETTDVGQTLGYNIGGNFQSA | 150 |
| Mu50 | RMIWPFQYNIGLTTKDPNVSLINYLPKNKIETTDVGQTLGYNIGGNFQSA | 150 |
| TCH_70 | RMIWPFQYNIGLTTKDPNVSLINYLPKNKIETTDVGQTLGYNIGGNFQSA | 150 |
| MRSA131 | RMIWPFQYNIGLTTKDPNVSLINYLPKNKIETTDVGQTLGYNIGGNFQSA | 150 |
| | ************************************************** | |
| LukE Consensus Sequence | RMIWPFQYNIGLTTKDPNVSLINYLPKNKIETTDVGQTLGYNIGGNFQSA | |
| | | |
| Newman | PSIGGNGSFNYSKTISYTQKSYVSEVDKQNSKSVKWGVKANEFVTPDGKK | 200 |
| MW2 | PSIGGNGSFNYSKTISYTQKSYVSEVDKQNSKSVKWGVKANEFVTPDGKK | 200 |
| USA_300_FPR3757 | PSIGGNGSFNYSKTISYTQKSYVSEVDKQNSKSVKWGVKANEFVTPDGKK | 200 |
| COL | PSIGGNGSFNYSKTISYTQKSYVSEVDKQNSKSVKWGVKANEFVTPDGKK | 200 |
| USA_300_TCH1516 | PSIGGNGSFNYSKTISYTQKSYVSEVDKQNSKSVKWGVKANEFVTPDGKK | 200 |
| N315 | PSIGGNGSFNYSKTISYTQKSYVSEVDKQNSKSVKWGVKANEFVTPDGKK | 200 |
| D30 | PSIGGNGSFNYSKTISYTQKSYVSEVDKQNSKSVKWGVKANEFVTPDGKK | 200 |
| Mu50 | PSIGGNGSFNYSKTISYTQKSYVSEVDKQNSKSVKWGVKANEFVTPDGKK | 200 |
| TCH_70 | PSIGGNGSFNYSKTISYTQKSYVSEVDKQNSKSVKWGVKANEFVTPDGKK | 200 |
| MRSA131 | PSIGGNGSFNYSKTISYTQKSYVSEVDKQNSKSVKWGVKANEFVTPDGKK | 200 |
| | ************************************************** | |
| LukE Consensus Sequence | PSIGGNGSFNYSKTISYTQKSYVSEVDKQNSKSVKWGVKANEFVTPDGKK | |
| | | |
| Newman | SAHDRYLFVQSPNGPTGSAREYFAPDNQLPPLVQSGFNPSFITTLSHEKG | 250 |
| MW2 | SAHDRYLFVQSPNGPTGSAREYFAPDNQLPPLVQSGFNPSFITTLSHEKG | 250 |
| USA_300_FPR3757 | SAHDRYLFVQSPNGPTGSAREYFAPDNQLPPLVQSGFNPSFITTLSHEKG | 250 |
| COL | SAHDRYLFVQSPNGPTGSAREYFAPDNQLPPLVQSGFNPSFITTLSHEKG | 250 |
| USA_300_TCH1516 | SAHDRYLFVQSPNGPTGSAREYFAPDNQLPPLVQSGFNPSFITTLSHEKG | 250 |
| N315 | SAHDRYLFVQSPNGPTGSAREYFAPDNQLPPLVQSGFNPSFITTLSHEKG | 250 |
| D30 | SAHDRYLFVQSPNGPTGSAREYFAPDNQLPPLVQSGFNPSFITTLSHEKG | 250 |
| Mu50 | SAHDRYLFVQSPNGPTGSAREYFAPDNQLPPLVQSGFNPSFITTLSHEKG | 250 |
| TCH_70 | SAHDRYLFVQSPNGPTGSAREYFAPDNQLPPLVQSGFNPSFITTLSHEKG | 250 |
| MRSA131 | SAHDRYLFVQSPNGPTGSAREYFAPDNQLPPLVQSGFNPSFITTLSHEKG | 250 |
| | ************************************************** | |
| LukE Consensus Sequence | SAHDRYLFVQSPNGPTGSAREYFAPDNQLPPLVQSGFNPSFITTLSHEKG | |
| | | |
| Newman | SSDTSEFEISYGRNLDITYATLFPRTGIYAERKHNAFVNRNFVVRYEVNW | 300 |
| MW2 | SSDTSEFEISYGRNLDITYATLFPRTGIYAERKHNAFVNRNFVVRYEVNW | 300 |
| USA_300_FPR3757 | SSDTSEFEISYGRNLDITYATLFPRTGIYAERKHNAFVNRNFVVRYEVNW | 300 |
| COL | SSDTSEFEISYGRNLDITYATLFPRTGIYAERKHNAFVNRNFVVRYEVNW | 300 |
| USA_300_TCH1516 | SSDTSEFEISYGRNLDITYATLFPRTGIYAERKHNAFVNRNFVVRYEVNW | 300 |
| N315 | SSDTSEFEISYGRNLDITYATLFPRTGIYAERKHNAFVNRNFVVRYEVNW | 300 |
| D30 | SSDTSEFEISYGRNLDITYATLFPRTGIYAERKHNAFVNRNFVVRYEVNW | 300 |
| Mu50 | SSDTSEFEISYGRNLDITYATLFPRTGIYAERKHNAFVNRNFVVRYEVNW | 300 |
| TCH_70 | SSDTSEFEISYGRNLDITYATLFPRTGIYAERKHNAFVNRNFVVRYEVNW | 300 |
| MRSA131 | SSDTSEFEISYGRNLDITYATLFPRTGIYAERKHNAFVNRNFVVRYEVNW | 300 |
| | ************************************************** | |
| LukE Consensus Sequence | SSDTSEFEISYGRNLDITYATLFPRTGIYAERKHNAFVNRNFVVRYEVNW | |
| | | |
| Newman | KTHEIKVKGHN | 311 |
| MW2 | KTHEIKVKGHN | 311 |
| USA_300_FPR3757 | KTHEIKVKGHN | 311 |
| COL | KTHEIKVKGHN | 311 |
| USA_300_TCH1516 | KTHEIKVKGHN | 311 |
| N315 | KTHEIKVKGHN | 311 |
| D30 | KTHEIKVKGHN | 311 |
| Mu50 | KTHEIKVKGHN | 311 |
| TCH_70 | KTHEIKVKGHN | 311 |
| MRSA131 | KTHEIKVKGHN | 311 |
| | *********** | |
| LukE Consensus Sequence | KTHEIKVKGHN | |

→ Depicts the start of the secreted LukE protein

TABLE 2

LukD Amino Acid Sequence Alignment

→

| | | | |
|---|---|---|---|
| Newman | MKMKKLVKSSVASSIALLLLSNTVDAAQHITPVSEKKVDDKITLYKTTAT | 50 | SEQ ID NO: 12 |
| MW2 | MKMKKLVKSSVASSIALLLLSNTVDAAQHITPVSEKKVDDKITLYKTTAT | 50 | SEQ ID NO: 13 |
| USA_300_FPR3757 | MKMKKLVKSSVASSIALLLLSNTVDAAQHITPVSEKKVDDKITLYKTTAT | 50 | SEQ ID NO: 14 |
| COL | MKMKKLVKSSVASSIALLLLSNTVDAAQHITPVSEKKVDDKITLYKTTAT | 50 | SEQ ID NO: 15 |
| USA_300_TCH1516 | MKMKKLVKSSVASSIALLLLSNTVDAAQHITPVSEKKVDDKITLYKTTAT | 50 | SEQ ID NO: 16 |
| MRSA131 | MKMKKLVKSSVASSIALLLLSNTVDAAQHITPVSEKKVDDKITLYKTTAT | 50 | SEQ ID NO: 17 |
| TCH_70 | MKMKKLVKSSVASSIALLLLSNTVDAAQHITPVSEKKVDDKITLYKTTAT | 50 | SEQ ID NO: 18 |
| D30 | MKMKKLVKSSVASSIALLLLSNTVDAAQHITPVSEKKVDDKITLYKTTAT | 50 | SEQ ID NO: 19 |

TABLE 2 -continued

LukD Amino Acid Sequence Alignment

| | | | |
|---|---|---|---|
| N315 | MKMKKLVKSSVASSIALLLLSNTVDAAQHITPVSEKKVDDKITLYKTTAT | 50 | SEQ ID NO: 20 |
| Mu50 | MKMKKLVKSSVASSIALLLLSNTVDAAQHITPVSEKKVDDKITLYKTTAT | 50 | SEQ ID NO: 21 |
| | ************************************************** | | |
| LukD Consensus Sequence | MKMKKLVKSSVASSIALLLLSNTVDAAQHITPVSEKKVDDKITLYKTTAT | 50 | SEQ ID NO: 22 |

| | | |
|---|---|---|
| Newman | SDNDKLNISQILTENFIKDKSYDKDTLVLKAAGNINSGYKKPNPKDYNYS | 100 |
| MW2 | SDNDKLNISQILTENFIKDKSYDKDTLVLKAAGNINSGYKKPNPKDYNYS | 100 |
| USA_300_FPR3757 | SDNDKLNISQILTENFIKDKSYDKDTLVLKAAGNINSGYKKPNPKDYNYS | 100 |
| COL | SDNDKLNISQILTENFIKDKSYDKDTLVLKAAGNINSGYKKPNPKDYNYS | 100 |
| USA_300_TCH1516 | SDNDKLNISQILTENFIKDKSYDKDTLVLKAAGNINSGYKKPNPKDYNYS | 100 |
| MRSA131 | SDNDKLNISQILTENFIKDKSYDKDTLVLKAAGNINSGYKKPNPKDYNYS | 100 |
| TCH_70 | SDNDKLNISQILTENFIKDKSYDKDTLVLKAAGNINSGYKKPNPKDYNYS | 100 |
| D30 | SDNDKLNISQILTENFIKDKSYDKDTLVLKAAGNINSGYKKPNPKDYNYS | 100 |
| N315 | SDNDKLNISQILTENFIKDKSYDKDTLVLKAAGNINSGYKKPNPKDYNYS | 100 |
| Mu50 | SDNDKLNISQILTENFIKDKSYDKDTLVLKAAGNINSGYKKPNPKDYNYS | 100 |
| | ************************************************** | |
| LukD Consensus Sequence | SDNDKLNISQILTENFIKDKSYDKDTLVLKAAGNINSGYKKPNPKDYNYS | |

| | | |
|---|---|---|
| Newman | QFYWGGKYNVSVSSESNDAMNVVDYAPKNQNEEFQVQQTLGYSYGGDINI | 150 |
| MW2 | QFYWGGKYNVSVSSESNDAMNVVDYAPKNQNEEFQVQQTLGYSYGGDINI | 150 |
| USA_300_FPR3757 | QFYWGGKYNVSVSSESNDAMNVVDYAPKNQNEEFQVQQTLGYSYGGDINI | 150 |
| COL | QFYWGGKYNVSVSSESNDAMNVVDYAPKNQNEEFQVQQTLGYSYGGDINI | 150 |
| USA_300_TCH1516 | QFYWGGKYNVSVSSESNDAMNVVDYAPKNQNEEFQVQQTLGYSYGGDINI | 150 |
| MRSA131 | QFYWGGKYNVSVSSESNDAMNVVDYAPKNQNEEFQVQQTLGYSYGGDINI | 150 |
| TCH_70 | QFYWGGKYNVSVSSESNDAMNVVDYAPKNQNEEFQVQQTLGYSYGGDINI | 150 |
| D30 | QFYWGGKYNVSVSSESNDAMNVVDYAPKNQNEEFQVQQTLGYSYGGDINI | 150 |
| N315 | QFYWGGKYNVSVSSESNDAMNVVDYAPKNQNEEFQVQQTLGYSYGGDINI | 150 |
| Mu50 | QFYWGGKYNVSVSSESNDAMNVVDYAPKNQNEEFQVQQTLGYSYGGDINI | 150 |
| | ************************************************** | |
| LukD Consensus Sequence | QFYWGGKYNVSVSSESNDAMNVVDYAPKNQNEEFQVQQTLGYSYGGDINI | |

| | | |
|---|---|---|
| Newman | SNGLSGGLNGSKSFSETINYKQESYRTTIDRKTNHKSIGWGVEAHKIMNN | 200 |
| MW2 | SNGLSGGLNGSKSFSETINYKQESYRTTIDRKTNHKSIGWGVEAHKIMNN | 200 |
| USA_300_FPR3757 | SNGLSGGLNGSKSFSETINYKQESYRTTIDRKTNHKSIGWGVEAHKIMNN | 200 |
| COL | SNGLSGGLNGSKSFSETINYKQESYRTTIDRKTNHKSIGWGVEAHKIMNN | 200 |
| USA_300_TCH1516 | SNGLSGGLNGSKSFSETINYKQESYRTTIDRKTNHKSIGWGVEAHKIMNN | 200 |
| MRSA131 | SNGLSGGLNGSKSFSETINYKQESYRTTIDRKTNHKSIGWGVEAHKIMNN | 200 |
| TCH_70 | SNGLSGGLNGSKSFSETINYKQESYRTTIDRKTNHKSIGWGVEAHKIMNN | 200 |
| D30 | SNGLSGGLNGSKSFSETINYKQESYRTTIDRKTNHKSIGWGVEAHKIMNN | 200 |
| N315 | SNGLSGGLNGSKSFSETINYKQESYRTTIDRKTNHKSIGWGVEAHKIMNN | 200 |
| Mu50 | SNGLSGGLNGSKSFSETINYKQESYRTTIDRKTNHKSIGWGVEAHKIMNN | 200 |
| | ************************************************** | |
| LukD Consensus Sequence | SNGLSGGLNGSKSFSETINYKQESYRTTIDRKTNHKSIGWGVEAHKIMNN | |

| | | |
|---|---|---|
| Newman | GWGPYGRDSYDPTYGNELFLGGRQSSSNAGQNFLPTHQMPLLARGNFNPE | 250 |
| MW2 | GWGPYGRDSYDPTYGNELFLGGRQSSSNAGQNFLPTHQMPLLARGNFNPE | 250 |
| USA_300_FPR3757 | GWGPYGRDSYDPTYGNELFLGGRQSSSNAGQNFLPTHQMPLLARGNFNPE | 250 |
| COL | GWGPYGRDSYDPTYGNELFLGGRQSSSNAGQNFLPTHQMPLLARGNFNPE | 250 |
| USA_300_TCH1516 | GWGPYGRDSYDPTYGNELFLGGRQSSSNAGQNFLPTHQMPLLARGNFNPE | 250 |
| MRSA131 | GWGPYGRDSYDPTYGNELFLGGRQSSSNAGQNFLPTHQMPLLARGNFNPE | 250 |
| TCH_70 | GWGPYGRDSYDPTYGNELFLGGRQSSSNAGQNFLPTHQMPLLARGNFNPE | 250 |
| D30 | GWGPYGRDSYDPTYGNELFLGGRQSSSNAGQNFLPTHQMPLLARGNFNPE | 250 |
| N315 | GWGPYGRDSYDPTYGNELFLGGRQSSSNAGQNFLPTHQMPLLARGNFNPE | 250 |
| Mu50 | GWGPYGRDSYDPTYGNELFLGGRQSSSNAGQNFLPTHQMPLLARGNFNPE | 250 |
| | ************************************************** | |
| LukD Consensus Sequence | GWGPYGRDSYDPTYGNELFLGGRQSSSNAGQNFLPTHQMPLLARGNFNPE | |

| | | |
|---|---|---|
| Newman | FISVLSHKQNDTKKSKIKVTYQREMDRYTNQWNRLHWVGNNYKNQNTVTF | 300 |
| MW2 | FISVLSHKQNDTKKSKIKVTYQREMDRYTNQWNRLHWVGNNYKNQNTVTF | 300 |
| USA_300_FPR3757 | FISVLSHKQNDTKKSKIKVTYQREMDRYTNQWNRLHWVGNNYKNQNTVTF | 300 |
| COL | FISVLSHKQNDTKKSKIKVTYQREMDRYTNQWNRLHWVGNNYKNQNTVTF | 300 |
| USA_300_TCH1516 | FISVLSHKQNDTKKSKIKVTYQREMDRYTNQWNRLHWVGNNYKNQNTVTF | 300 |
| MRSA131 | FISVLSHKQNDTKKSKIKVTYQREMDRYTNQWNRLHWVGNNYKNQNTVTF | 300 |
| TCH_70 | FISVLSHKQNDTKKSKIKVTYQREMDRYTNQWNRLHWVGNNYKNQNTVTF | 300 |
| D30 | FISVLSHKQNDTKKSKIKVTYQREMDRYTNQWNRLHWVGNNYKNQNTVTF | 300 |
| N315 | FISVLSHKQNDTKKSKIKVTYQREMDRYTNQWNRLHWIGNNYKNQNTVTF | 300 |
| Mu50 | FISVLSHKQNDTKKSKIKVTYQREMDRYTNQWNRLHWIGNNYKNQNTVTF | 300 |
| | ***********************************:********* | |
| LukD Consensus Sequence | FISVLSHKQNDTKKSKIKVTYQREMDRYTNQWNRLHWXGNNYKNQNTVTF | |

| | | |
|---|---|---|
| Newman | TSTYEVDWQNHTVKLIGTDSKETNPGV | 327 |
| MW2 | TSTYEVDWQNHTVKLIGTDSKETNPGV | 327 |
| USA_300_FPR3757 | TSTYEVDWQNHTVKLIGTDSKETNPGV | 327 |
| COL | TSTYEVDWQNHTVKLIGTDSKETNPGV | 327 |
| USA_300_TCH1516 | TSTYEVDWQNHTVKLIGTDSKETNPGV | 327 |
| MRSA131 | TSTYEVDWQNHTVKLIGTDSKETNPGV | 327 |
| TCH_70 | TSTYEVDWQNHTVKLIGTDSKETNPGV | 327 |
| D30 | TSTYEVDWQNHTVKLIGTDSKETNPGV | 327 |

TABLE 2 -continued

LukD Amino Acid Sequence Alignment

```
N315              TSTYEVDWQNHTVKLIGTDSKETNPGV                  327
Mu50              TSTYEVDWQNHTVKLIGTDSKETNPGV                  327
                  **************************
LukD Consensus Sequence TSTYEVDWQNHTVKLIGTDSKETNPGV
```

→ Depicts the start of the secreted LukE protein Depicts the start of the secreted LukD protein Thus, unless indicated to the contrary, both the immature and the mature forms of native LukE and LukD, and the sequences having less than 100% similarity with native LukE and LukD (i.e., native sequences and analogs alike, collectively referred to herein as "LukE" and "LukD") may be used in the methods of the present invention.

LukE and LukD proteins and polypeptides of the invention may differ from the native polypeptides designated as SEQ ID NOS:1-11 and 12-22 respectively, in terms of one or more additional amino acid insertions, substitutions or deletions, e.g., one or more amino acid residues within SEQ ID NOS:1-22 may be substituted by another amino acid of a similar polarity, which acts as a functional equivalent, resulting in a silent alteration. That is to say, the change relative to the native sequence would not appreciably diminish the basic properties of native LukE or LukD. Any such analog of LukE or LukD may be screened in accordance with the protocols disclosed herein (e.g., the cell toxicity assay and the membrane damage assay) to determine if it maintains native LukE or LukD activity. Substitutions within these leukocidins may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

In other embodiments, non-conservative alterations (e.g., one or amino acid substitutions, deletions and/or additions) can be made for purposes of detoxifying LukE and/or LukD. The detoxified LukE and LukD may be used in the active vaccine compositions. Molecular alterations can be accomplished by methods well known in the art, including primer extension on a plasmid template using single stranded templates (Kunkel et al., *Proc. Acad. Sci., USA* 82:488-492 (1985), which is hereby incorporated by reference in its entirety), double stranded DNA templates (Papworth, et al., Strategies 9(3):3-4 (1996), which is hereby incorporated by reference in its entirety), and by PCR cloning (Braman, J. (ed.), *IN VITRO MUTAGENESIS PROTOCOLS,* 2nd ed. Humana Press, Totowa, N.J. (2002), which is hereby incorporated by reference in its entirety). Methods of determining whether a given molecular alteration in LukE and LukD reduces LukE/D cytotoxicity are described herein.

In a preferred embodiment of the present invention, a highly purified LukE/LukD preparation is utilized. Examples include LukE and LukD proteins or polypeptides purified from the various strains exemplified in Tables 1 and 2. Methods of purifying LukE and LukD toxins are known in the art (Gravet et al., "Characterization of a Novel Structural Member, LukE-LukD, of the Bi-Component Staphylococcal Leucotoxins Family," *FEBS* 436: 202-208 (1998), which is hereby incorporated by reference in its entirety). As used herein, "isolated" protein or polypeptide refers to a protein or polypeptide that has been separated from other proteins, lipids, and nucleic acids with which it is naturally associated with. Purity can be measured by any appropriate standard method, for example, by column chromatography, polyacrylamide gel electrophoresis, of HPLC analysis. An isolated protein or polypeptide of the invention can be purified from a natural source, produced by recombinant DNA techniques, or by chemical methods.

In one embodiment of this aspect of the present invention, the isolated LukE or LukD protein or polypeptide thereof of the composition is linked to an immunogenic carrier molecule. In some cases, the immunogenic carrier molecule may be covalently or non-covalently bound to the immunogenic protein or peptide. Exemplary immunogenic carrier molecules include, but are not limited to, bovine serum albumin, chicken egg ovalbumin, keyhole limpet hemocyanin, tetanus toxoid, diphtheria toxoid, thyro globulin, a pneumococcal capsular polysaccharide, CRM 197, and a meningococcal outer membrane protein.

In certain embodiments of the present invention, the composition may further contain one or more additional *S. aureus* antigens. Suitable *S. aureus* antigens include, without limitation, alpha hemolysin antigen, protein A, a serotype 336 polysaccharide antigen, coagulase, clumping factor A, clumping factor B, a fibronectin binding protein, a fibrinogen binding protein, a collagen binding protein, an elastin binding protein, a MEW analogous protein, a polysaccharide intracellular adhesion, beta hemolysin, delta hemolysin, gamma hemolysin, Panton-Valentine leukocidin, leukocidin A, leukocidin B, leukocidin M, exfoliative toxin A, exfoliative toxin B, V8 protease, hyaluronate lyase, lipase, staphylokinase, an enterotoxin, toxic shock syndrome toxin-1, poly-N-succinyl beta-1→6 glucosamine, catalase, beta-lactamase, teichoic acid, peptidoglycan, a penicillin binding protein, chemotaxis inhibiting protein, complement inhibitor, Sbi, Type 5 antigen, Type 8 antigen, lipoteichoic acid, and microbial surface proteins that recognize host proteins (e.g., iron surface determinents, serine-aspartate repeat proteins).

In accordance with this aspect of the invention, the composition may further comprise one or more adjuvants. Suitable adjuvants are known in the art and include, without limitation, flagellin, Freund's complete or incomplete adjuvant, aluminum hydroxide, lysolecithin, pluronic polyols, polyanions, peptides, oil emulsion, dinitrophenol, iscomatrix, and liposome polycation DNA particles.

In embodiments wherein the therapeutic composition is intended for use as an active vaccine, the LukE and/or LukD proteins or polypeptides may be altered so as to exhibit reduced toxicity. Alterations for purposes of reducing toxicity of LukE and LukD include chemical treatment (e.g., modification of specific amino acid residues as described supra) or conjugation to another moiety (e.g., to another bacterial antigen, such as a bacterial polysaccharide or a bacterial glycoprotein). Chemical alterations to other *S. aureus* toxins for purposes of detoxification (or reducing toxicity) are known. Methods of determining whether a given alteration reduces LukE or LukD toxicity are known in the art and/or described herein.

The therapeutic compositions of the present invention are prepared by formulating LukE and LukD with a pharmaceutically acceptable carrier and optionally a pharmaceutically acceptable excipient. As used herein, the terms "pharmaceutically acceptable carrier" and "pharmaceutically acceptable excipient" (e.g., additives such as diluents, immunostimulants, adjuvants, antioxidants, preservatives and solubilizing agents) are nontoxic to the cell or mammal being exposed thereto at the dosages and concentrations employed. Examples of pharmaceutically acceptable carriers include water, e.g., buffered with phosphate, citrate and another organic acid. Representative examples of pharmaceutically acceptable excipients that may be useful in the present invention include antioxidants such as ascorbic acid; low molecular weight (less than about 10 residues) polypeptides; proteins, such as serum albumin, gelatin, or immunoglobulins; adjuvants (selected so as to avoid adjuvant-induced toxicity, such as a β-glucan as described in U.S. Pat. No. 6,355,625, which is hereby incorporated by reference in its entirety, or a granulocyte colony stimulating factor (GCSF)); hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants such as TWEEN®, polyethylene glycol (PEG), and PLURONICS®.

Therapeutic compositions of the present invention may be prepared for storage by mixing the active ingredient(s) having the desired degree of purity with the pharmaceutically acceptable carrier and optional excipient and/or additional active agent, in the form of lyophilized formulations or aqueous solutions.

Another aspect of the present invention relates to a method of immunizing against a *Staphylococcus aureus* infection in a subject. This method involves administering a composition of the present invention, in an amount effective to immunize against *S. aureus* infection in the subject. A suitable subject for treatment in accordance with this aspect of the present invention is a subject at risk of developing a *S. aureus* infection.

In accordance with this aspect of the invention, a therapeutically effective amount of the composition for administration to a subject to immunize against *S. aureus* infection is the amount necessary to generate a humoral (i.e., antibody mediated) immune response. Preferably, administration of a therapeutically effective amount of the composition of the present invention induces a neutralizing immune response against *S. aureus* in the subject. To effectuate an effective immune response in a subject, the composition may further contain one or more additional *S. aureus* antigens or an adjuvant as described supra. In an alternative embodiment of this aspect of the invention, the adjuvant is administered separately from the composition to the subject, either before, after, or concurrent with administration of the composition of the present invention.

Modes of administration and therapeutically effective dosing related to this aspect of the invention are described infra.

Another aspect of the present invention relates to a composition comprising a therapeutically effective amount of an antibody selected from the group consisting of a Leukocidin E (LukE) antibody, a Leukocidin D (LukD) antibody, or a combination thereof, and a pharmaceutically acceptable carrier.

In one embodiment of this aspect of the present invention, the composition comprises a LukE antibody or antigen-binding fragment thereof. Suitable LukE antibodies include those antibodies recognizing one or more epitopes in the amino acid sequence of SEQ ID NO:11. Likewise, in another embodiment, the composition comprises a LukD antibody or antigen-binding fragment thereof. Suitable LukD antibodies recognize one or more epitopes in the amino acid sequence of SEQ ID NO:22. In another embodiment of the invention, the composition comprises both LukE and LukD antibodies or antigen binding fragments thereof. Preferably, the composition comprises one or more neutralizing LukE and/or LukD antibodies. In yet another embodiment, the anti-LukE and/or anti-LukD antibody composition is multivalent in that it also contains an antibody that specifically binds another bacterial antigen (and that optionally neutralizes the other bacterial antigen). For example, the composition may comprise one or more antibodies that recognize one or more additional *S. aureus* antigens, including, without limitation, one or more of the *S. aureus* antigens described supra.

For purposes of the present invention, the term "antibody" includes monoclonal antibodies, polyclonal antibodies, antibody fragments, genetically engineered forms of the antibodies, and combinations thereof. More specifically, the term "antibody," which is used interchangeably with the term "immunoglobulin," includes full length (i.e., naturally occurring or formed by normal immunoglobulin gene fragment recombinatorial processes) immunoglobulin molecules (e.g., an IgG antibody) and immunologically active fragments thereof (i.e., including the specific binding portion of the full-length immunoglobulin molecule), which again may be naturally occurring or synthetic in nature. Accordingly, the term "antibody fragment" includes a portion of an antibody such as $F(ab')_2$, $F(ab)_2$, Fab', Fab, Fv, scFv and the like. Regardless of structure, an antibody fragment binds with the same antigen that is recognized by the full-length antibody, and, in the context of the present invention, specifically binds LukE, LukD, or a LukE/D complex. Methods of making and screening antibody fragments are well-known in the art.

In the present invention, the anti-LukE antibodies may have some degree of cross-reactivity with other *Staphylococcus* leukocidin S-subunits such as HlgC, LukS-PVL, HlgA, LukS-I, LukA, and LukM. Likewise, in some embodiments, the anti-LukD antibodies of the present invention may have some degree of cross-reactivity with other *Staphylococcus* leukocidin F-subunits such as LukF'-PV, LukF-PV, LukB, LukF-I, and HlgB. Anti-LukE and/or anti-LukD antibodies may inhibit or reduce LukE activity and LukD activity, respectively. In some embodiments, the anti-LukE and/or anti-LukD antibodies neutralize (e.g., substantially eliminate) LukE and LukD activity, respectively.

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CH1, CH2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of VL and VH, which are supported by less variable regions called framework variable regions. The inventive antibodies include IgG monoclonal antibodies as well as antibody fragments or engineered forms. These are, for example, Fv fragments, or proteins wherein the CDRs and/or variable domains of the exemplified antibodies are engineered as single-chain antigen-binding proteins.

The portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker. The peptide linkers used to produce the single chain antibodies are typically flexible peptides, selected to assure that the proper three-dimensional folding of the VL and VH domains occurs. The linker is generally 10 to 50 amino acid residues, and in some cases is shorter, e.g., about 10 to 30 amino acid residues, or 12 to 30 amino acid residues, or even 15 to 25 amino acid residues. An example of such linker peptides includes repeats of four glycine residues followed by a serine residue.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Fab (Fragment, antigen binding) refers to the fragments of the antibody consisting of the VL, CL, VH, and CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')$_2$ fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement mediated cytotoxicity and antibody-dependent cellular-cytotoxicity (ADCC). For antibodies such as IgA and IgM, which are complexes of multiple IgG-like proteins, complex formation requires Fc constant domains.

Finally, the hinge region separates the Fab and Fc portions of the antibody, providing for mobility of Fabs relative to each other and relative to Fc, as well as including multiple disulfide bonds for covalent linkage of the two heavy chains.

Antibody "specificity" refers to selective recognition of the antibody for a particular epitope of an antigen. The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational". In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another, i.e., noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen.

Monoclonal antibodies of the present invention may be murine, human, humanized or chimeric. A humanized antibody is a recombinant protein in which the CDRs of an antibody from one species; e.g., a rodent, rabbit, dog, goat, horse, or chicken antibody (or any other suitable animal antibody), are transferred into human heavy and light variable domains. The constant domains of the antibody molecule are derived from those of a human antibody. Methods for making humanized antibodies are well known in the art. Chimeric antibodies preferably have constant regions derived substantially or exclusively from human antibody constant regions and variable regions derived substantially or exclusively from the sequence of the variable region from a mammal other than a human. The chimerization process can be made more effective by also replacing the variable regions—other than the hyper-variable regions or the complementarity—determining regions (CDRs), of a murine (or other non-human mammalian) antibody with the corresponding human sequences. The variable regions other than the CDRs are also known as the variable framework regions (FRs). Yet other monoclonal antibodies of the present invention are bi-specific, in that they have specificity for both LukE and LukD. Bispecific antibodies are preferably human or humanized.

The above-described antibodies can be obtained in accordance with standard techniques. For example, LukE, LukD, or an immunologically active fragment of LukE or LukD can be administered to a subject (e.g., a mammal such as a human or mouse). The leukocidins can be used by themselves as immunogens or they can be attached to a carrier protein or other objects, such as sepharose beads. After the mammal has produced antibodies, a mixture of antibody producing cells, such as splenocytes, are isolated, from which polyclonal antibodies may be obtained. Monoclonal antibodies may be produced by isolating individual antibody-producing cells from the mixture and immortalizing them by, for example, fusing them with tumor cells, such as myeloma cells. The resulting hybridomas are preserved in culture and the monoclonal antibodies are harvested from the culture medium.

Another aspect of the present invention is directed to a method of preventing a S. aureus infection and/or S. aureus-associated conditions in a subject. This method comprises administering a composition of the invention comprising an antibody selected from the group consisting of a Leukocidin E (LukE) antibody, a Leukocidin D (LukD) antibody, or a combination thereof, in an amount effective to prevent S. aureus infection and/or S. aureus associated condition in the subject.

In accordance with this aspect of the invention, S. aureus-associated conditions include, without limitation, skin wounds and infections, tissue abscesses, folliculitis, osteomyelitis, pneumonia, scalded skin syndrome, septicemia, septic arthritis, myocarditis, endocarditis, and toxic shock syndrome.

Modes of administration and therapeutically effective dosing related to this aspect of the invention are described infra.

A further aspect of the present invention is directed to a method of treating a S. aureus infection and/or S. aureus-associated conditions in a subject. This method involves administering a composition comprising one or more inhibitors of LukE/D mediated cytotoxicity in an amount effective to treat the S. aureus infection and/or the S. aureus associated condition in the subject.

In accordance with this aspect of the invention, suitable inhibitors of LukE/D mediated cytotoxicity include protein or peptide inhibitors, nucleic acid inhibitors, or small molecule inhibitors.

In one embodiment of the invention, the inhibitor of LukE/D mediated cytotoxicity is a LukE inhibitor. Suitable LukE inhibitors include antibodies or antibody fragments recognizing an epitope in the amino acid sequence of SEQ ID NO:11. In another embodiment of the invention, the inhibitor of LukE/D mediated cytotoxicity is a LukD inhibitor. Suitable LukD inhibitors include antibodies or antibody fragments recognizing an epitope in the amino acid sequence of SEQ ID NO:22.

In another embodiment of this aspect of the present invention, the inhibitor of LukE/D mediated cytotoxicity inhibits LukE and LukD interaction. Suitable inhibitors in accordance with this embodiment include anti-LukE and/or LukD antibodies that target the interacting regions of LukE or LukD. Alternatively, suitable inhibitors include small molecules that bind to the interacting regions of LukE and/or LukD. These interacting regions may include amino acids 3-13 of SEQ ID NO:11, amino acids 32-47 of SEQ ID NO:11, amino acids 126-139 of SEQ ID NO:11, amino acids 151-156 of SEQ ID NO:11, and amino acids 272-283 of SEQ ID NO:11. The interacting regions may also include amino acids: 3-17 of SEQ ID NO:22, amino acids 33-51 of SEQ ID NO:22, amino acids 94-113 of SEQ ID NO:22, amino acids 115-131 of SEQ ID NO:22, and amino acids 229-2741 of SEQ ID NO:22.

In another embodiment of this aspect of the present invention, the inhibitor of LukE/D mediated cytotoxicity inhibits LukE/D from binding to the plasma membrane of leukocytes. Suitable inhibitors include antibodies or small molecules recognizing the epitopes of LukE and/or LukD that interact with the plasma membrane of leukocytes. The regions of LukE and LukD that interact with the plasma membrane include the amino acids encompassing the rim domain of LukE. These amino acid regions include LukE amino acids 57-75 of SEQ ID NO:11, amino acids 82-99 of SEQ ID NO:11, amino acids 162-198 of SEQ ID NO:11, amino acids 190-235 of SEQ ID NO:11, amino acids 263-284 of SEQ ID NO:11, and amino acids 230-273 of SEQ ID NO:11 and LukD amino acids 59-75 of SEQ ID NO:22, amino acids 170-220 of SEQ ID NO:22, and amino acids 253-268 of SEQ ID NO:22. Accordingly, antibodies recognizing these epitopes of LukE and/or LukD are particularly suitable for this embodiment of the invention.

In another embodiment of this aspect of the present invention, the inhibitor of LukE/D mediated cytotoxicity is an agent that prevents LukE/D oligomer complex formation, an agent that blocks LukE/LukD mediated pore formation, or an agent that blocks the LukE/LukD pore. In accordance with this embodiment, suitable inhibitors of the LukE/LukD mediated pore include cyclodextrin and related compounds, and any other pore inhibitor including protein or peptide inhibitors, nucleic acid inhibitors, or small molecule inhibitors.

In yet another embodiment of this aspect of the present invention, the inhibitor of LukE/D mediated cytotoxicity is an agent that modulates the expression and/or activity of an endogenous repressor or activator of LukE/D expression. Accordingly, administering an agent that induces or mimics the expression and or activity of Repressor of Toxins ("Rot"), which is a repressor of lukE and lukD expression, inhibits LukE/D mediated cytotoxicity by virtue of blocking toxin production. Suitable agents that mimic Rot expression and activity and are suitable for use in the methods of the present invention are disclosed in U.S. Patent Application Publication No. 2003/0171563 to McNamara, which is hereby incorporated by reference in its entirety. Likewise, administering an agent that inhibits the expression or activity of SaeRS, which is an activator of lukE and lukD expression, inhibits LukE/D mediated cytotoxicity by virtue of blocking toxin production.

For purposes of this and other aspects of the invention, the target "subject" encompasses any animal, preferably a mammal, more preferably a human. In the context of administering a composition of the invention for purposes of preventing a S. aureus infection in a subject, the target subject encompasses any subject that is at risk of being infected by S. aureus. Particularly susceptible subjects include infants and juveniles, as well as immunocompromised juvenile, adults, and elderly adults. However, any infant, juvenile, adult, or elderly adult or immunocompromised individual at risk for S. aureus infection can be treated in accordance with the methods of the present invention. In the context of administering a composition of the invention for purposes of treating a S. aureus infection in a subject, the target subject population encompasses any subject infected with S. aureus. Particularly suitable subjects include those at risk of infection or those infected with methicillin-resistant S. aureus (MRSA) or methicillin sensitive S. aureus (MSSA).

In the context of using therapeutic compositions of the present invention to prevent a S. aureus infection, either via active or passive vaccination, the concentration of LukE and LukD proteins or polypeptides or anti-LukE and anti-LukD antibodies in the composition are adequate to achieve the prevention of S. aureus infection, particularly the prevention of S. aureus in susceptible populations. In the context of using therapeutic compositions to treat a S. aureus infection, the amounts of anti-LukE and anti-LukD antibodies or agents that inhibit LukE/D mediated cytotoxicity are capable of achieving a reduction in a number of symptoms, a decrease in the severity of at least one symptom, or a delay in the further progression of at least one symptom, or even a total alleviation of the infection.

Therapeutically effective amounts of LukE, LukD, anti-LukE and anti-LukD antibodies, and agents that inhibit LukE/D mediated cytotoxicity can be determined in accordance with standard procedures, which take numerous factors into account, including, for example, the concentrations of these active agents in the composition, the mode and frequency of administration, the severity of the S. aureus infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer LukE and LukD or anti-LukE and anti-LukD antibodies, until a dosage is reached that provides the desired or required prophylactic or therapeutic effect. The progress of this therapy can be easily monitored by conventional assays.

Therapeutically effective amounts of LukE and LukD for immunization will depend on whether adjuvant is co-administered, with higher dosages being required in the absence of adjuvant. The amount of LukE and LukD for administration sometimes varies from 1 µg-500 µg per patient and more usually from 5-500 µg per injection for human administration. Occasionally, a higher dose of 1-2 mg per injection is used. Typically about 10, 20, 50 or 100 µg is used for each human injection. Preferably, the amounts of LukE and LukD are substantially the same. The timing of injections can vary significantly from once a day, to once a year, to once a decade. Generally an effective dosage can be monitored by obtaining a fluid sample from the subject, generally a blood serum sample, and determining the titer of antibody developed against the LukE and LukD protein or polypeptide, using methods well known in the art and readily adaptable to the specific antigen to be measured. Ideally, a sample is taken prior to initial dosing and subsequent samples are taken and titered after each immunization. Generally, a dose or dosing schedule which provides a detectable titer at least four times greater than control or "background" levels at a serum dilution of 1:100 is desirable, where background is defined relative to a control serum or relative to a plate background in ELISA assays.

Therapeutically effective amount of the LukE and LukD antibody compositions typically are at least 50 mg composition per kilogram of body weight (mg/kg), including at least 100 mg/kg, at least 150 mg/kg, at least 200 mg/kg, at least 250 mg/kg, at least 500 mg/kg, at least 750 mg/kg and at least 1000 mg/kg, per dose or on a daily basis. Dosages for monoclonal antibody compositions might tend to be lower, such as about one-tenth of non-monoclonal antibody compositions, such as at least about 5 mg/kg, at least about 10 mg/kg, at least about 15 mg/kg, at least about 20 mg/kg, or at least about 25 mg/kg. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the subject. Alternatively, antibody can be administered as a sustained release formulation, in which case less frequent administration is required. Dosage and frequency vary depending on the half-life of the antibody in the subject. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated, and preferably until the subject shows partial or complete amelioration of symptoms of disease.

The therapeutic compositions of the present invention can be administered as part of a combination therapy in conjunction with another active agent, depending upon the nature of the S. aureus infection that is being treated. Such additional active agents include anti-infective agents, antibiotic agents, and antimicrobial agents. Representative anti-infective agents that may be useful in the present invention include vancomycin and lysostaphin. Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art. See, e.g., MERCK MANUAL OF DIAGNOSIS AND THERAPY, Section 13, Ch. 157, $100^{th}$ Ed. (Beers & Berkow, eds., 2004), which is hereby incorporated by reference in its entirety. The anti-inflammatory, anti-infective, antibiotic and/or antimicrobial agents may be combined prior to administration, or administered concurrently (as part of the same composition or by way of a different composition) or sequentially with the inventive therapeutic compositions of the present invention. In certain embodiments, the administering is repeated. The subject may be an infant, juvenile, adult, or elderly adult. The subject may also be an immuno-compromised juvenile, adult, or elderly adult.

Therapeutic compositions of the present invention may be administered in a single dose, or in accordance with a multi-dosing protocol. For example, relatively few doses of the therapeutic composition are administered, such as one or two doses. In embodiments that include conventional antibiotic therapy, which generally involves multiple doses over a period of days or weeks, the antibiotics can be taken one, two or three or more times daily for a period of time, such as for at least 5 days, 10 days or even 14 or more days, while the antibody composition is usually administered only once or twice. However, the different dosages, timing of dosages and relative amounts of the therapeutic composition and antibiotics can be selected and adjusted by one of ordinary skill in the art.

Compositions for of the present invention can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intra-arterial, intracranial, or intradermal injections are also effective in generating an immune response.

The pharmaceutical agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

A further aspect of the present invention relates to a method of predicting severity of an *S. aureus* infection. This method involves culturing *S. aureus* obtained from an infected subject via a fluid or tissue sample from the subject and quantifying LukE and/or LukD expression in the cultured *S. aureus*. The quantified amounts of LukE and/or LukD in the sample from the subject are compared to the amount of LukE and/or LukD in a control sample which produces little or undetectable amounts of LukE and/or LukD and the severity of the *S. aureus* infection is predicted based on said comparing.

Another aspect of the present invention relates to a method of treating a subject with a *S. aureus* infection. This method involves culturing *S. aureus* obtained from an infected subject via a fluid or tissue sample from the subject and quantifying LukE and/or LukD expression in the cultured *S. aureus*. The quantified amounts of LukE and/or LukD in the sample from the subject are compared to the amount of LukE and/or LukD in a control sample which produces little or undetectable amounts of LukE and/or LukD, and a suitable treatment for the subject is determined based on this comparison. The method further involves administering the determined suitable treatment to the subject to treat the *S. aureus* infection.

In accordance with these aspects of the invention, quantifying LukE and LukD expression in the sample from the subject involves measuring the level of LukE and/or LukD mRNA expression or protein production. Methods of quantifying mRNA and protein expression levels in a sample are well known in the art. An increased level of LukE and/or LukD mRNA expression or protein production in the sample from the subject compared to the control sample indicates or predicts the subject has or will have a more severe *S. aureus* infection. Likewise, an increased level of LukE and/or LukD mRNA expression or protein production in the sample from the subject indicates that a suitable treatment for the subject having the infection involves one or more agents that inhibit LukE/D mediated cytotoxicity. Suitable agents for inhibiting LukE/D cytotoxicity are discloses supra.

Another aspect of the present invention relates to a method of identifying inhibitors of LukE/D cytotoxicity. This method involves providing a cell population, a preparation containing LukE and LukD, and a candidate LukE/D inhibitor. The cell population is exposed to the preparation containing LukE and LukD in the presence and absence of the candidate inhibitor, and LukE/D mediated cytotoxicity is measured in the presence and in the absence of the candidate inhibitor. The measured amount of cytotoxicity in the presence and in the absence of the candidate inhibitor is compared and an inhibitor of LukE/D cytotoxicity is identified based on this comparison.

In accordance with this aspect of the invention, anti-LukE and anti-LukD antibodies, and fragments thereof, as well as other potential therapeutic moieties (e.g., small organic molecules) may be screened to evaluate their ability to inhibit LukE/D mediated cytotoxicity. As described below, various methods have been designed to identify agents that inhibit some aspect of the cascade of events that leads to LukE/D mediated cytotoxicity and lysis of human leukocytes. The methods are also designed to identify altered forms of LukE and LukD that possess reduced toxicity relative to their native counterparts. The targeted events that are part of the cascade include for example, binding of LukE and/or LukD to leukocyte plasma membranes, interaction between LukE and LukD (LukE/D oligomerization), and blockage of the membrane pore formed by the LukE/D oligomer. The assay formats generally require human leukocytes (or LukE or LukD membrane-binding portion thereof), suitable culture medium, and purified LukE and LukD.

A person of skill will appreciate that the following protocols are merely illustrative and that various operating parameters such as reaction conditions, choice of detectable label and apparati (e.g., instrumentation for detection and quantification) may be varied as deemed appropriate.

The following methods are generally directed to identifying agents that inhibit LukE/D cytotoxicity, without necessarily revealing the exact event in the cascade that is affected.

To identify inhibitors of LukE/D cytotoxicity, human leukocytes (e.g., THP-1) may be plated in 384-well clear-bottom black tissue culture treated plate (Corning) at $5 \times 10^3$ cells/well in a final volume of 50 µl of RPMI (Gibco) supplemented with 10% of heat inactivated fetal bovine serum (FBS). Cells may then be contacted/mixed/reacted/treated with the test compound/molecule (~5 µl/different concentrations) and then intoxicated with LukE and LukD, which in preferred embodiments are substantially purified (5 µl of a ~0.01-5 µM solution), preferably added together, under culture conditions to allow for intoxication of the leukocytes by LukE and LukD, e.g., for 1 hr at 37° C., 5% $CO_2$. As controls, cells may be treated with culture medium (100% viable) and with 0.1% v/v Triton X100 (100% death).

In these embodiments, cells treated as described above may then be incubated with a dye to monitor cell viability such as CellTiter (Promega) (which enables determination of cell viability via absorbance by measuring the number of viable cells in a culture by quantification of the metabolic activity of the cells) and incubated for an additional time period (e.g., about 2 hrs at 37° C., 5% $CO_2$). Cell viability may then be determined such as by measuring the colorimetric reaction at 492 nm using a plate reader e.g., Envision 2103 Multi-label Reader (Perkin-Elmer). Percent viable cells may be calculated such as by using the following equation: % Viability=100×[($Ab_{492}$Sample−$Ab_{492}$TritonX)/($Ab_{492}$Tissue culture media). An increase in the 100% viability suggests inhibition of LukE/D mediated cytotoxicity.

A variation of this assay is referred to as a membrane damage assay. In these embodiments, cells treated as described above (e.g., up to and including treating of the cells with test compound/molecule and then intoxicating the cells with purified LukE and LukD), may then be incubated with a cell-impermeable fluorescent dye such as SYTOX green (0.1 µM; Invitrogen) (in accordance with manufacturer's instructions) and incubated e.g., for an additional 15 minutes at room temperature in the dark. Fluorescence, as an indicator of membrane damage, may then be measured using a plate reader such as Envision 2103 Multilabel Reader (Perkin-Elmer) at Excitation 485 nm, Emission 535 nm. A decrease in fluorescence suggests inhibition of LukE/D cytotoxicity.

In another variation of this assay, cells treated as described above (e.g., up to and including treating of the cells with test compound and then intoxicating the cells with purified LukE and LukD), may then be incubated with a marker of cell lysis and incubated for an additional period of time at room temperature in the dark. The marker of cell lysis is measured, and a decrease in the level of cell lysis in the presence of the compound indicates inhibition of LukE/D cytotoxicity.

Together these assays will facilitate the identification of compounds that inhibit or reduce LukE/D cytotoxic effects towards leukocyte cells.

Additional methods may be used, independently or in conjunction with the methods described above, particularly if the above methods reveal inhibitory activity, that will enable a person skilled in the field to determine more precisely what event in the biochemical cascade is being affected or targeted by the agent. These events include binding of LukE and/or LukD to leukocyte membranes, binding of LukE to LukD (LukE/D oligomerization), and blockage of the membrane pore formed by the LukE/D oligomers.

Another aspect of the present invention is directed to a method of identifying inhibitors of LukE, LukD, and/or LukE/D binding to target cells. This method involves providing a population of leukocytes or other target cells, a preparation containing a detectably labeled LukE, LukD, or LukE/D, and a candidate inhibitor. The cell population is exposed to the preparation containing the detectably labeled LukE, LukD, or LukE/D in the presence and absence of the candidate inhibitor, and labeled LukE, LukD, or LukE/D binding to the leukocyte population is measured in the presence and absence of the candidate inhibitor. The measured amount of LukE, LukD, or LukE/D binding in the presence and in the absence of the candidate inhibitor is compared and an inhibitor of LukE, LukD, or LukE/D-leukocyte binding is identified based on this comparison.

To screen for inhibitors that block or reduce LukE, LukD or LukE/D binding to target cells, which is the first step in the intoxication process, human leukocytes (e.g., THP-1 cells) may be plated in 384-well flat-bottom tissue culture treated plates (Corning) at 2.5×10³ cells/well in a final volume of 50 µl of RPMI (Gibco) supplemented with 10% of heat inactivated fetal bovine serum (FBS). Cells may then be treated with the test compound/molecule (~5 µl/different concentrations) and incubated with purified, fluorescently labeled LukE, LukD and/or LukE/D (e.g., FITC, Cy3, Cy5, APC, PE) 5 µl of a ~0.01-5 µM solution for 1 hr at 4° C., 5% $CO_2$. To evaluate the efficacy of the tested compounds/molecules, the cell-associated fluorescence may be measured as an indicator of LukE, LukD, or LukE/D binding to cells e.g., using an automated fluorescence microscopic imaging system designed for high content screening and high content analysis (e.g., Cellomics ArrayScan HCS Reader (Thermo Scientific) (Excitation 485 nm, Emission 535 nm)). In accordance with this aspect of the invention, a decrease in LukE, LukD, or LukE/D-leukocyte binding in the presence of the candidate inhibitor compared to in its absence identifies a binding inhibitor.

To screen for inhibitors that block or reduce LukE/LukD interaction, which is the second step in the intoxication process, human leukocytes (e.g., THP-1 cells) may be plated in 384-well flat-bottom tissue culture treated plates (Corning) at 2.5×10³ cells/well in a final volume of 50 µl of RPMI (Gibco) supplemented with 10% of heat inactivated fetal bovine serum (FBS). Cells may then be treated with the test compound/molecule and then intoxicated with a mixture of purified LukE and purified LukD where LukD is fluorescently-labeled with a fluorescence molecule such as FITC, Cy3, Cy5, APC, and PE, and allowed to stand to complete the intoxication process (e.g., for 1 hr at 37° C., 5% $CO_2$). To evaluate the efficacy of the tested compounds/molecules, cell-associated LukD-FITC fluorescence may be measured as an indicator of LukE/LukD-FITC interaction, using for example, an automated fluorescence microscopic imaging system designed for high content screening and high content analysis (e.g., a Cellomics ArrayScan HCS Reader (Thermo Scientific) (Excitation 485 nm, Emission 535 nm). Similar experiments could be performed using fluorescently-labeled LukE instead of LukD.

Another aspect of the present invention relates to a method of identifying inhibitors of LukE/D mediated pore formation. This method involves providing a population of leukocytes, a preparation containing LukE and LukD, and a candidate inhibitor. The leukocyte population is exposed to the preparation containing LukE and LukD in the presence and absence of the candidate inhibitor, and pore formation on the leukocyte population is measured in the presence and absence of the candidate inhibitor. The measured amount of pore formation in the presence and in the absence of the candidate inhibitor is compared, and an inhibitor of LukE/D mediated pore formation is identified based on that comparison.

To screen for inhibitors that block or inhibit formation of the LukE/D pore, the effector molecule that leads to cell lysis, human leukocytes (e.g., THP-1 cells) may be plated in 384-well clear-bottom black tissue culture treated plate (Corning) at 2.5×10³ cells/well in a final volume of 50 µl of RPMI (Gibco) supplemented with 10% of heat inactivated fetal bovine serum (FBS). Cells may then be treated with the test compound/molecule (~5 µl containing different concentrations) and then intoxicated with purified LukE and LukD or LukE/D (~0.01-5 μM) for 15 minutes at 37° C., 5% $CO_2$. As controls, cells may be treated with culture medium (negative control) and with 0.1% v/v TritonX100 (positive control).

To directly evaluate LukE/D pores on the surface of host cells, an ethidium bromide (EB) influx assay may be used. EB is a small-cationic dye that is impermeable to healthy host cells. Upon formation of cationic pores by LukE/D, EB enters the cells and binds to DNA, which results in fluorescence. Cell treated in this fashion may then be incubated with EB (5 μM) for an additional 5 minutes at room temperature in the dark. To evaluate the efficacy of the tested compounds/molecules in inhibiting LukE/D pore formation the fluorescence may be measured as an indicator of pore formation, using a plate-reader such as the Envision 2103 Multilabel Reader (Perkin-Elmer) at Excitation 530 nm, Emission 590 nm. This assay will facilitate the identification of molecules that can block or inhibit the LukE/D pore, which will alleviate LukE/D mediated toxicity.

To directly evaluate LukE/D pores on the surface of host cells, an ethidium bromide (EB) influx assay may be used. EB is a small-cationic dye that is impermeable into healthy host cells. Upon formation of cationic pores by LukE/D, EB enters the cells and binds to DNA, which results in fluorescence (see e.g., FIG. 5E). Cells treated with an agent causing LukE/D pore formation may then be incubated with EB (5 μM) for an additional 5 minutes at room temperature in the dark. To evaluate the efficacy of the tested compounds/ molecules in inhibiting LukE/D pore formation the fluorescence may be measured as an indicator of pore formation, using a plate-reader such as the Envision 2103 Multilabel Reader (Perkin-Elmer) at Excitation 530 nm, Emission 590 nm. This assay will facilitate the identification of molecules that can block or inhibit the LukE/D pore, which will alleviate LukE/D mediated toxicity.

The candidate compounds utilized in the assays described herein may be essentially any compound or composition suspected of being capable of affecting biological functions or interactions. The compound or composition may be part of a library of compounds or compositions. Alternatively, the compound or compositions may be designed specifically to interact or interfere with the biological activity of LukE, LukD, or LukE/D of the present invention.

EXAMPLES

The following examples are provided to illustrate embodiments of the present invention but are by no means intended to limit its scope.

Example 1—Inactivation of Rot Enhances the Virulence of a S. aureus Strain Lacking Agr In recent studies it has been found that S. aureus mutant strains that lack both the master regulator known as the accessory gene regulator ("Agr") and the transcription factor repressor of toxins ("Rot") (i.e., Δag Δrrot) exhibit enhanced virulence in a murine model of systemic infection compared to the highly attenuated Δagr mutant. While a Δagr single deletion mutant is highly attenuated for virulence as measured by survival over time post-infection, an Δagr Δrot double mutant displays virulence characteristics similar to that of the parent strain (WT Newman) (FIG. 1A). It was speculated that the increased virulence observed in an Δagr Δrot double mutant might be due to enhanced expression of S. aureus leukotoxins as many of these toxins are believed to be regulated in an Agr-Rot dependent manner. Indeed, immunoblot analysis of the toxins produced by S. aureus Wild Type, Δagr, and the Δagr Δrot mutant strains confirmed the hypothesis as a number of toxins were restored to WT levels in an Δagr Δrot double mutant (FIG. 1B). Strikingly, it was observed that LukE/D is highly over-produced by the Δagr Δrot strain compared to the other toxins (FIG. 1B). This data demonstrates that repression of key virulence factors by Rot is critical to optimal virulence potential in S. aureus and that the leukotoxin LukE/D is heavily repressed in a Rot-dependent manner, more so than other leukotoxins.

Figures 2A, 2B, 2C:
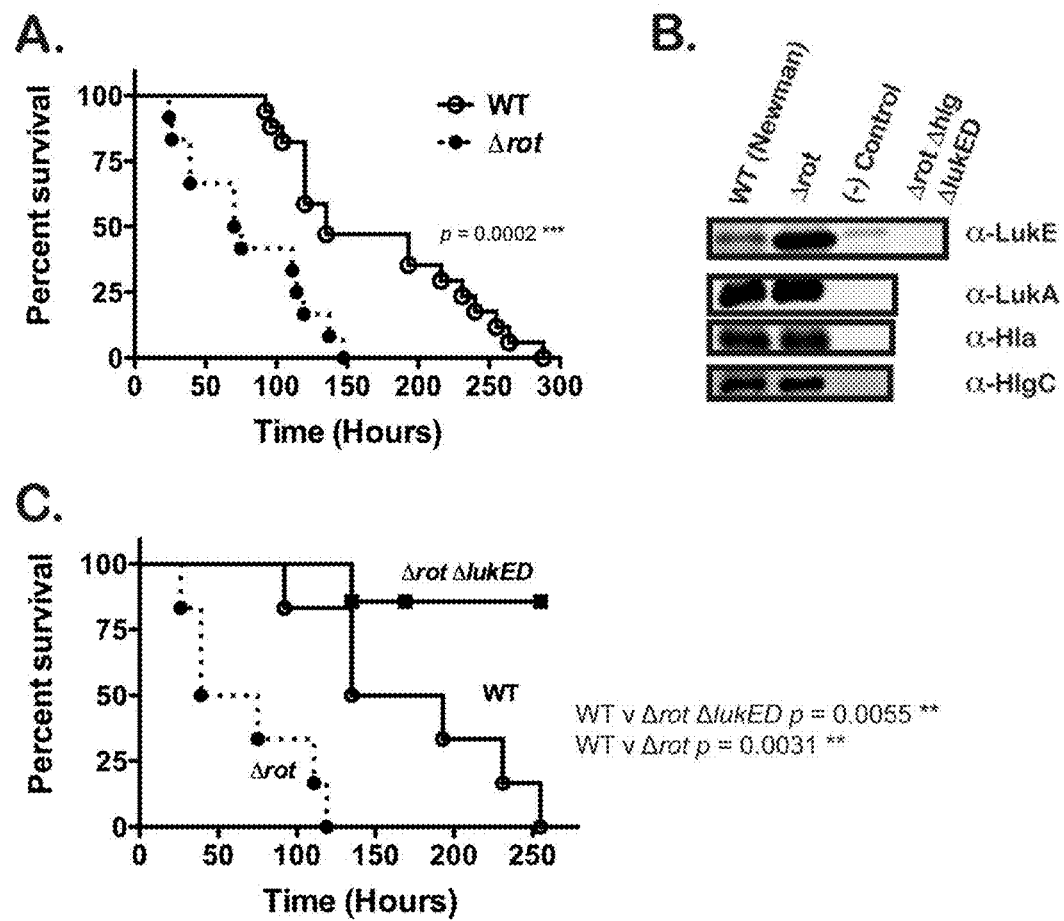
FIGS. 2A-2C illustrate that deletion of rot alone results in hypervirulence in animals, a phenotype caused by derepression and resultant overproduction of LukE/D. The survival curve of FIG. 2A shows the hypervirulence of a Δrot mutant compared to the parent WT strain. Survival of mice was monitored after intravenous injection with ~1×10$^7$ CFU of *S. aureus* WT and Δrot strains. Total number of mice per group: WT, N=17; Δrot, N=12. The production of LukE/D is increased in the absence of the transcriptional repressor Rot, while the production of other leukotoxins is largely unaffected. Shown in the immunoblots of FIG. 2B are protein samples from TCA precipitated bacterial culture supernatants (grown for 5 hours in RPMI+CAS) of the following strains: WT, and Δrot. Negative control lanes contain TCA precipitated supernatant from respective toxin-rot double mutants (Δrot ΔlukE/D, Δrot ΔlukA/B, Δrot Δhla, and Δrot ΔhlgACB). Δrot ΔlukE/D ΔhlgACB triple mutant exoproteins were also probed in all the LukE immunoblots as a control for LukE antibody cross-reactivity. As indicated by the survival curve of FIG. 2C, the hypervirulence of a Δrot mutant is due to increased production of LukE/D. Survival of mice was monitored after intravenous injection with ~1×10$^7$ CFU of S. aureus WT, Δrot, and Δrot ΔlukE/D. Statistical significance between survival curves was determined using the Log-rank (Mantel-Cox) test. , p≤0.005; *, p≤0.0005.

Example 2—LukE/D Contributes to the Enhanced Virulence Exhibited by a S. aureus Strain Lacking Rot The results described in FIGS. 1A-1B indicated that inactivation of rot in an agr$^+$ strain might also result in increased virulence, possibly in a LukE/D dependent manner. As with the Δagr Δrot double mutant (FIG. 1A), it was observed that a Δrot single deletion mutant also resulted in enhanced virulence in a murine model of systemic infection, as evidenced by the decrease in percent survival of animals infected with Δrot compared to those infected with WT (FIG. 2A). Earlier observations demonstrated that Rot is likely a major repressor of the leukotoxin LukE/D. To confirm these findings in the context of the single Δrot deletion mutant, immunoblot were performed. These experiments revealed that indeed LukE/D is highly produced in the absence of rot, contrary to LukAB, γ-hemolysin (HlgC), or α-toxin (Hla; FIG. 2B). These findings further strengthened the supposition that LukE/D is the major Rot-repressed factor responsible for the increase in virulence of a Δrot mutant and that LukE/D could play a significant role in the in vivo pathogenesis of S. aureus. To determine whether LukE/D overproduction was responsible for the enhanced pathogenic phenotype of Δrot, a Δrot ΔlukE/D double mutant was constructed and its virulence in a mouse model of infection was assessed. The Δrot ΔlukE/D double mutant was significantly compromised for virulence as evidenced by the striking reduction in mortality compared to both WT as well as the Δrot mutant (FIG. 2C). These results demonstrate that LukE/D is a major Rot-repressed factor that is critical for the hypervirulence associated with a Δrot mutant and that LukE/D may be a major contributor to disease in general. These data further indicate that drugs that enhance Rot mediated repression of target genes will reduce S. aureus pathogenesis.

Figures 3A, 3B:
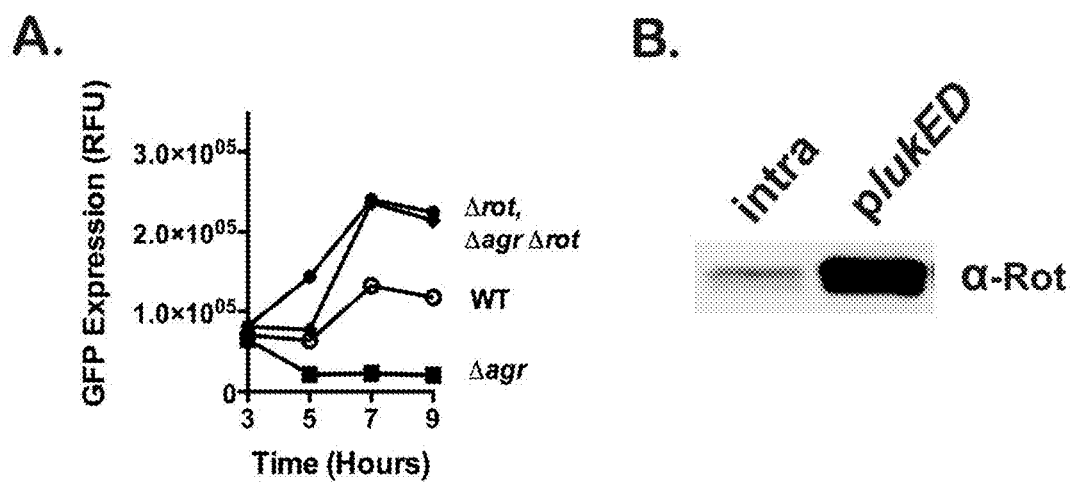
FIGS. 3A-3B show that Rot binds to the lukE/D promoter and represses gene expression.

Example 3—Rot Represses LukE/D Expression by Directly Binding to the LukE/D Promoter To further examine the influence of Rot on lukE/D gene expression, transcriptional fusions of the lukE/D promoter region to a gene that encodes for the green fluorescent protein (GFP) were constructed and fluorescence was measured over time in broth culture using WT, Δagr, Δrot, and Δagr Δrot strains. As suspected, gene expression of lukE/D was increased over that of WT in strains lacking Rot, while strains expressing large amounts of Rot (Δagr mutants display increased Rot levels) were decreased in expression. To assess whether repression of lukE/D by Rot is direct, the ability of Rot to bind to the lukE/D promoter was examined using a promoter pull-down strategy. Bacterial whole cell lysates were incubated with lukE/D promoter DNA or nonspecific intergenic DNA bound to magnetic beads. Immunoblot of bound proteins demonstrated that Rot indeed binds to the lukE/D promoter in a specific manner (FIG. 3B). These results implicate Rot as a direct repressor of lukE/D gene expression. Alterations in Rot levels could thus substantially increase or decrease the production of LukE/D and by consequence modulate the virulence potential of *S. aureus*.

Example 4—LukE/D Significantly Contributes to *S. aureus* Pathogenesis

Figures 4A, 4B, 4C, 4D, 4E, 4F:
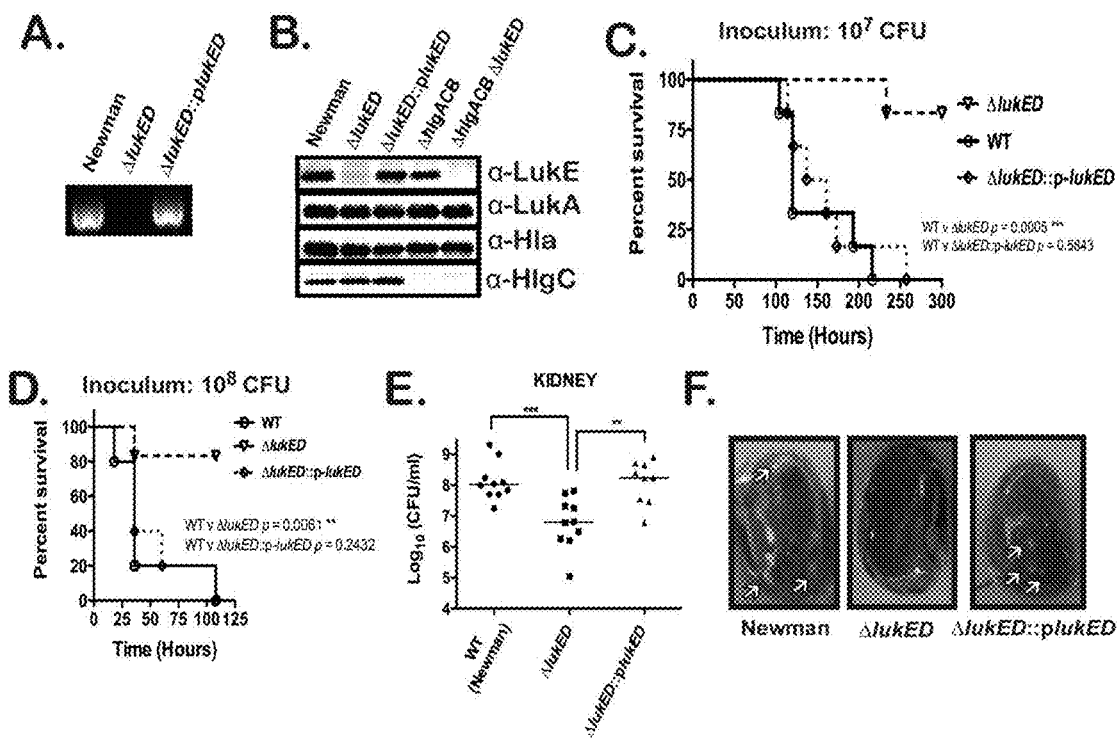
FIGS. 4A-4F illustrate that a ΔlukE/D single mutant is significantly attenuated for virulence in a mouse model of systemic infection.

Not only does a Δrot ΔlukE/D double deletion mutant eliminate the hypervirulence associated with a rot deletion, it also substantially reduces virulence overall (compare WT survival to Δrot ΔlukE/D survival FIG. 3B). To test whether LukE/D plays a major role in the pathogenesis of *S. aureus* septicemic infection, a ΔlukE/D mutant in the strain Newman was constructed (FIGS. 4A and 4B) and the impact of lukE/D deletion alone on virulence was examined. Survival over time dramatically increased for mice infected with either $10^7$ or $10^8$ CFU of the ΔlukE/D mutant compared to the wild type. All wild type mice succumbed to infection by 250 hours at the $10^7$ dose (FIG. 4C) and by 100 hours at the $10^8$ dose (FIG. 4D). In both cases however, nearly 100% of mice infected with ΔlukE/D mutant survived until at least 300 hours post infection, a phenotype that is fully complemented with the ΔlukE/D::plukE/D strain (FIGS. 4B and 4C). In addition, bacterial burden to the kidney is reduced by 10-fold compared to the wild type or complemented strains (FIG. 4E) and abscess formation is significantly reduced (FIG. 4F). These results show that LukE/D is indeed a critical virulence factor for *S. aureus* systemic infection. Thus LukE/D is an attractive novel target for development of new therapeutics to counter *S. aureus* infection.

Example 5—LukE/D Targets and Kills Leukocytes

Figures 5A, 5B, 5C, 5D, 5E:
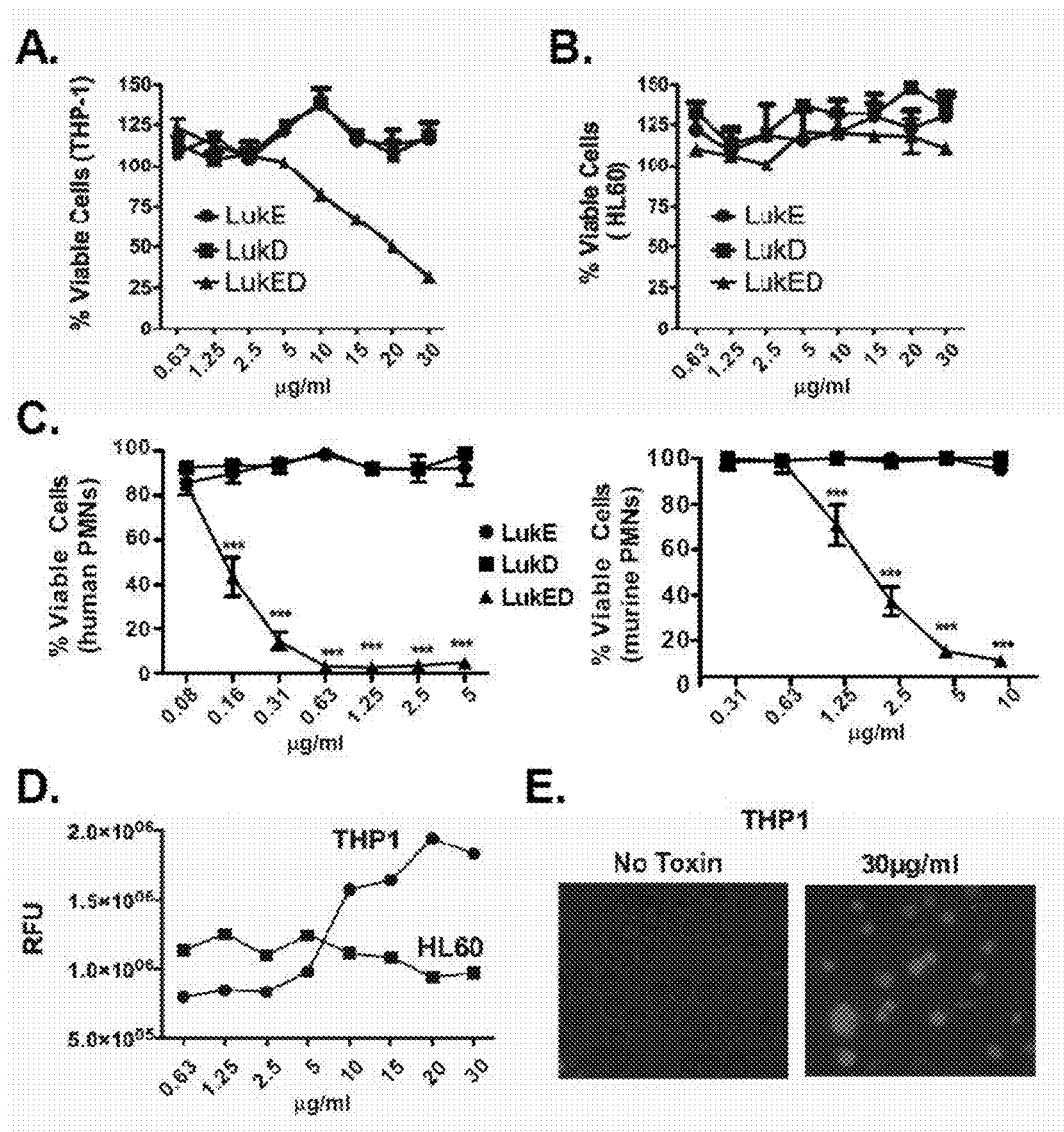
FIGS. 5A-5E show that LukE/D is toxic to and forms pores in human immune cells.

To determine the potential mechanism of action of LukE/D, recombinant LukE and LukD proteins from *E. coli* were expressed and purified. To test the potential toxicity of these proteins, human monocyte-like cells (THP-1s) and human promyelocytic leukemia cells (HL60s) were incubated with different concentrations of either individual subunits (i.e., LukE or LukD) or a mixture of LukE+LukD (LukE/D). Cells were intoxicated with a dose response of either LukE alone, LukD alone, or LukE/D and after 1 hour of intoxication CellTiter was added to measure the percent viable cells post-intoxication. The human monocyte-like cell line, THP-1, was uniquely sensitive to intoxication with both subunits of the toxin together but not individual subunits. The potency of the toxin towards the cells was dose dependent and strictly required the presence of both subunits (FIG. 5A). In contrast, HL60s were not affected by either subunit alone or incubated together (FIG. 5B). In addition to cell lines, the activity of LukE/D towards primary human and murine PMNs was also examined. Cells were intoxicated with a dose response of either LukE alone, LukD alone, or LukE/D and after 1 hour of intoxication CellTiter was added to measure the percent viable cells post-intoxication. LukE/D but not LukE or LukD was markedly cytotoxic towards PMNs from both human and mouse (FIG. 5C).

To examine the mechanism by which LukE/D is toxic to THP-1s, cells were intoxicated in the presence of ethidium bromide, a small cationic dye that is normally impermeable to host cell membranes, but can gain access to the cell via the toxin pore. Upon addition of both toxin subunits, ethidium bromide was rapidly taken up into cells as reflected by an increase in relative fluorescence compared to unintoxicated controls and intoxicated PMN-HL60s (FIGS. 5D and 5E). These experiments demonstrate that when together, LukE and LukD exhibit cytotoxicity toward specific human immune cell type, but not others, highlighting the specificity of this toxin.

Example 6—Antibodies Against LukE Potently Neutralized LukE/D Cytotoxicity

Figures 6A, 6B:
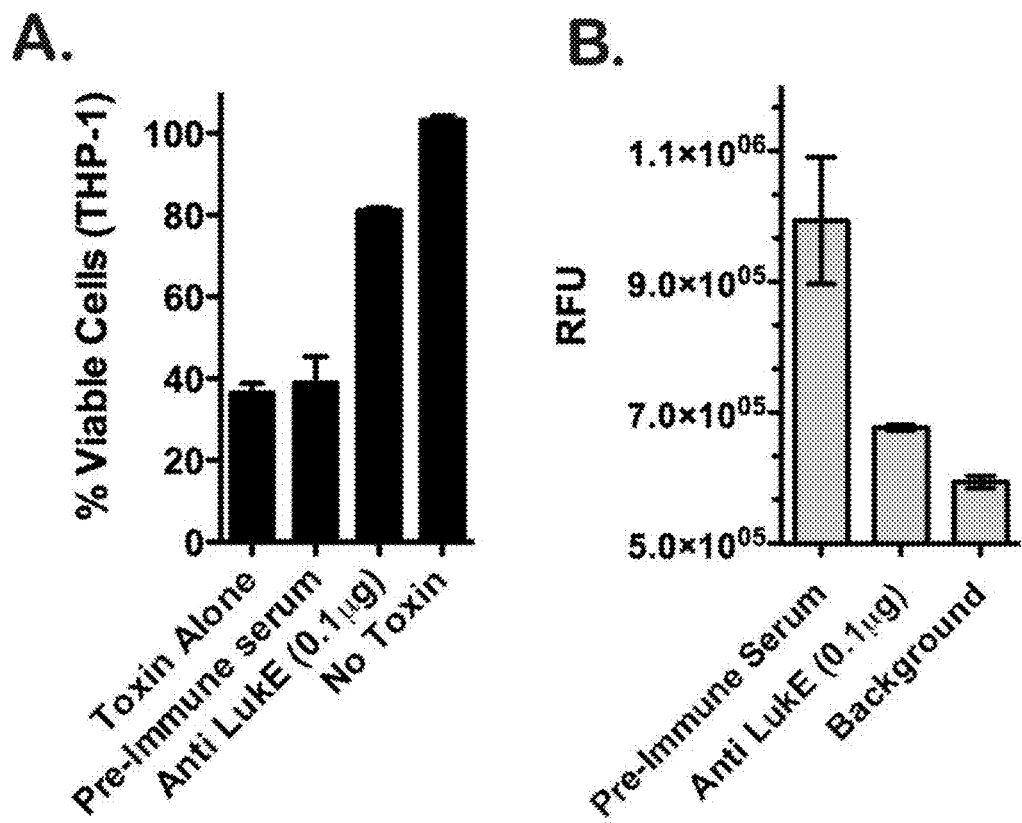
FIGS. 6A-6B illustrate that LukE/D cytotoxicity is neutralized with an affinity purified α-LukE polyclonal antibody. THP-1 cells were intoxicated with 1.5 µg of recombinant LukE/D following incubation with 0.1 µg α-LukE polyclonal antibody or pre-immune serum. Cell viability (FIG. 6A) and pore formation (FIG. 6B) were monitored using CellTiter and Ethidium bromide respectively. For CellTiter assays, cells treated with medium were set at 100% viability. Results represent the average of duplicate samples±standard deviation (S.D.).

To determine if polyclonal antibodies raised against LukE are capable of neutralizing LukE/D cytotoxicity, a neutralization assay was performed. Incubation of LukE/D with purified anti-LukE antibodies potently inhibited LukE/D mediated cytotoxicity towards THP-1 cells as measured by CellTiter (FIG. 6A). As shown in FIGS. 5A-5E, LukE/D appears to exert its toxic activity by forming permeable pores in the plasma membrane of target cells. To gain insight into the mechanism by which anti-LukE neutralizes LukE/D cytotoxicity, the formation of LukE/D pores in cells intoxicated with LukE/D in the presence of purified anti-LukE antibodies was monitored. It was observed that LukE/D pore formation was potently inhibited by the anti-LukE antibody (FIG. 6B). These data demonstrate that immunization with LukE generates anti-LukE neutralizing antibodies, suggesting LukE-specific antibodies could be a novel therapeutic to combat *S. aureus* infection.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A composition comprising:
one or more *Staphylococcus aureus*-specific monoclonal Leukocidin E (LukE) antibodies or binding fragments thereof, wherein said one or more monoclonal LukE antibodies and binding fragments thereof bind to an epitope within a region of LukE selected from amino acid residues 82-99 of SEQ ID NO: 11, amino acid residues 190-235 of SEQ ID NO: 11, and amino acid residues 263-284 of SEQ ID NO: 11; and
a pharmaceutically acceptable carrier.

2. The composition of claim 1, wherein the epitope is a linear epitope of LukE.

3. The composition of claim 1, wherein the epitope is a conformational epitope of LukE.

4. The composition of claim 1, wherein said composition further comprises one or more antibodies recognizing one or more *S. aureus* antigens selected from the group consisting of an alpha hemolysin antigen, gamma hemolysin, Panton-Valentine leukocidin, leukocidin A, leukocidin B, and microbial surface components recognizing host molecules.

5. The composition of claim 1, wherein the one or more monoclonal LukE antibodies or binding fragments thereof bind the epitope of LukE within amino acid residues 82-99 of SEQ ID NO: 11.

6. The composition of claim 1, wherein the one or more monoclonal LukE antibodies or binding fragments thereof bind the epitope of LukE within amino acid residues 190-235 of SEQ ID NO: 11.

7. The composition of claim 1, wherein the one or more monoclonal LukE antibodies or binding fragments thereof bind the epitope of LukE within amino acid residues 263-284 of SEQ ID NO: 11.

8. The composition of claim 1, wherein the one or more monoclonal LukE antibodies or binding fragments thereof are neutralizing antibodies or binding fragments thereof.

9. A monoclonal Leukocidin E (LukE) antibody or binding fragment thereof that binds to an epitope within a region of LukE selected from amino acid residues 82-99 of SEQ ID NO: 11, amino acid residues 190-235 of SEQ ID NO: 11, and amino acid residues 263-284 of SEQ ID NO: 11.

10. The monoclonal LukE antibody or binding fragment thereof of claim 9, wherein the epitope is a linear epitope of LukE.

11. The monoclonal LukE antibody or binding fragment thereof of claim 9, wherein the epitope is a conformational epitope of LukE.

12. The monoclonal LukE antibody or binding fragment thereof of claim 9, wherein the epitope is within amino acid residues 82-99 of SEQ ID NO: 11.

13. The monoclonal LukE antibody or binding fragment thereof of claim 9, wherein the epitope is within amino acid residues 190-235 of SEQ ID NO: 11.

14. The monoclonal LukE antibody or binding fragment thereof of claim 9, wherein the epitope is within amino acid residues 263-284 of SEQ ID NO: 11.

* * * * *

SEQUENCE LISTING

```
<160> NUMBER OF SEQ ID NOS: 22

<210> SEQ ID NO 1
<211> LENGTH: 311
<212> TYPE: PRT
<213> ORGANISM: Staphylococcus aureus

<400> SEQUENCE: 1

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30
```

-continued

```
Glu Asn Ile Gly Asp Gly Ala Glu Val Ile Lys Arg Thr Glu Asp Val
             35                  40                  45

Ser Ser Lys Lys Trp Gly Val Thr Gln Asn Val Gln Phe Asp Phe Val
 50                  55                  60

Lys Asp Lys Lys Tyr Asn Lys Asp Ala Leu Ile Val Lys Met Gln Gly
 65                  70                  75                  80

Phe Ile Asn Ser Arg Thr Ser Phe Ser Asp Val Lys Gly Ser Gly Tyr
                 85                  90                  95

Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
            130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
            195                 200                 205

Val Gln Ser Pro Asn Gly Pro Thr Gly Ser Ala Arg Glu Tyr Phe Ala
            210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
                260                 265                 270

Phe Pro Arg Thr Gly Ile Tyr Ala Glu Arg Lys His Asn Ala Phe Val
            275                 280                 285

Asn Arg Asn Phe Val Val Arg Tyr Glu Val Asn Trp Lys Thr His Glu
            290                 295                 300

Ile Lys Val Lys Gly His Asn
305                 310

<210> SEQ ID NO 2
<211> LENGTH: 311
<212> TYPE: PRT
<213> ORGANISM: Staphylococcus aureus

<400> SEQUENCE: 2

Met Phe Lys Lys Lys Met Leu Ala Ala Thr Leu Ser Val Gly Leu Ile
 1               5                  10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
             35                  40                  45

Ser Ser Lys Lys Trp Gly Val Thr Gln Asn Val Gln Phe Asp Phe Val
 50                  55                  60

Lys Asp Lys Lys Tyr Asn Lys Asp Ala Leu Ile Val Lys Met Gln Gly
 65                  70                  75                  80

Phe Ile Asn Ser Arg Thr Ser Phe Ser Asp Val Lys Gly Ser Gly Tyr
                 85                  90                  95
```

```
Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
    195                 200                 205

Val Gln Ser Pro Asn Gly Pro Thr Gly Ser Ala Arg Glu Tyr Phe Ala
210                 215                 220

Pro Asp Asn Gln Leu Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
    275                 280                 285

Asn Arg Asn Phe Val Val Arg Tyr Glu Val Asn Trp Lys Thr His Glu
290                 295                 300

Ile Lys Val Lys Gly His Asn
305                 310

<210> SEQ ID NO 3
<211> LENGTH: 311
<212> TYPE: PRT
<213> ORGANISM: Staphylococcus aureus

<400> SEQUENCE: 3

Met Phe Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
```

```
                145                 150                 155                 160
Tyr Ser Lys Thr Ile Ser Tyr Thr Gln Lys Ser Tyr Val Ser Glu Val
                    165                 170                 175

Asp Lys Gln Asn Ser Lys Ser Val Lys Trp Gly Val Lys Ala Asn Glu
                180                 185                 190

Phe Val Thr Pro Asp Gly Lys Lys Ser Ala His Asp Arg Tyr Leu Phe
            195                 200                 205

Val Gln Ser Pro Asn Gly Pro Thr Gly Ser Ala Arg Glu Tyr Phe Ala
        210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
290                 295                 300

Ile Lys Val Lys Gly His Asn
305                 310

<210> SEQ ID NO 4
<211> LENGTH: 311
<212> TYPE: PRT
<213> ORGANISM: Staphylococcus aureus

<400> SEQUENCE: 4

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205
```

```
Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
290                 295                 300

Ile Lys Val Lys Gly His Asn
305                 310

<210> SEQ ID NO 5
<211> LENGTH: 311
<212> TYPE: PRT
<213> ORGANISM: Staphylococcus aureus

<400> SEQUENCE: 5

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270
```

```
Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 6
<211> LENGTH: 311
<212> TYPE: PRT
<213> ORGANISM: Staphylococcus aureus

<400> SEQUENCE: 6

Met Phe Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310
```

```
<210> SEQ ID NO 7
<211> LENGTH: 311
<212> TYPE: PRT
<213> ORGANISM: Staphylococcus aureus

<400> SEQUENCE: 7
```

| | | | | | | | | | | | | | | | |
|---|---|---|---|---|---|---|---|---|---|---|---|---|---|---|---|
|Met|Phe|Lys|Lys|Lys|Met|Leu|Ala|Ala|Thr|Leu|Ser|Val|Gly|Leu|Ile|
|1| | | |5| | | | |10| | | | |15| |

Ala Pro Leu Ala Ser Pro Ile Gln Glu Ser Arg Ala Asn Thr Asn Ile
                20                  25                  30

Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
290                 295                 300

Ile Lys Val Lys Gly His Asn
305                 310

```
<210> SEQ ID NO 8
<211> LENGTH: 311
<212> TYPE: PRT
<213> ORGANISM: Staphylococcus aureus

<400> SEQUENCE: 8
```

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile

```
            20                  25                  30
Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 9
<211> LENGTH: 311
<212> TYPE: PRT
<213> ORGANISM: Staphylococcus aureus

<400> SEQUENCE: 9

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80
```

```
Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
            180                 185                 190

Phe Val Thr Pro Asp Gly Lys Lys Ser Ala His Asp Arg Tyr Leu Phe
        195                 200                 205

Val Gln Ser Pro Asn Gly Pro Thr Gly Ser Ala Arg Glu Tyr Phe Ala
    210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 10
<211> LENGTH: 311
<212> TYPE: PRT
<213> ORGANISM: Staphylococcus aureus

<400> SEQUENCE: 10

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
            20                  25                  30

Glu Asn Ile Gly Asp Gly Ala Glu Val Ile Lys Arg Thr Glu Asp Val
        35                  40                  45

Ser Ser Lys Lys Trp Gly Val Thr Gln Asn Val Gln Phe Asp Phe Val
    50                  55                  60

Lys Asp Lys Lys Tyr Asn Lys Asp Ala Leu Ile Val Lys Met Gln Gly
65                  70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
            100                 105                 110

Thr Thr Lys Asp Pro Asn Val Ser Leu Ile Asn Tyr Leu Pro Lys Asn
        115                 120                 125

Lys Ile Glu Thr Thr Asp Val Gly Gln Thr Leu Gly Tyr Asn Ile Gly
    130                 135                 140
```

```
Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
                180                 185                 190

Phe Val Thr Pro Asp Gly Lys Lys Ser Ala His Asp Arg Tyr Leu Phe
            195                 200                 205

Val Gln Ser Pro Asn Gly Pro Thr Gly Ser Ala Arg Glu Tyr Phe Ala
        210                 215                 220

Pro Asp Asn Gln Leu Pro Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
                260                 265                 270

Phe Pro Arg Thr Gly Ile Tyr Ala Glu Arg Lys His Asn Ala Phe Val
            275                 280                 285

Asn Arg Asn Phe Val Val Arg Tyr Glu Val Asn Trp Lys Thr His Glu
        290                 295                 300

Ile Lys Val Lys Gly His Asn
305                 310

<210> SEQ ID NO 11
<211> LENGTH: 311
<212> TYPE: PRT
<213> ORGANISM: Staphylococcus aureus

<400> SEQUENCE: 11

Met Phe Lys Lys Lys Met Leu Ala Ala Thr Leu Ser Val Gly Leu Ile
1               5                   10                  15

Ala Pro Leu Ala Ser Pro Ile Gln Glu Ser Arg Ala Asn Thr Asn Ile
                20                  25                  30

Glu Asn Ile Gly Asp Gly Ala Glu Val Ile Lys Arg Thr Glu Asp Val
            35                  40                  45

Ser Ser Lys Lys Trp Gly Val Thr Gln Asn Val Gln Phe Asp Phe Val
        50                  55                  60

Lys Asp Lys Lys Tyr Asn Lys Asp Ala Leu Ile Val Lys Met Gln Gly
65              70                  75                  80

Phe Ile Asn Ser Arg Thr Ser Phe Ser Asp Val Lys Gly Ser Gly Tyr
                85                  90                  95

Glu Leu Thr Lys Arg Met Ile Trp Pro Phe Gln Tyr Asn Ile Gly Leu
                100                 105                 110

Thr Thr Lys Asp Pro Asn Val Ser Leu Ile Asn Tyr Leu Pro Lys Asn
            115                 120                 125

Lys Ile Glu Thr Thr Asp Val Gly Gln Thr Leu Gly Tyr Asn Ile Gly
        130                 135                 140

Gly Asn Phe Gln Ser Ala Pro Ser Ile Gly Gly Asn Gly Ser Phe Asn
145                 150                 155                 160

Tyr Ser Lys Thr Ile Ser Tyr Thr Gln Lys Ser Tyr Val Ser Glu Val
                165                 170                 175

Asp Lys Gln Asn Ser Lys Ser Val Lys Trp Gly Val Lys Ala Asn Glu
                180                 185                 190

Phe Val Thr Pro Asp Gly Lys Lys Ser Ala His Asp Arg Tyr Leu Phe
```

```
                195                 200                 205
Val Gln Ser Pro Asn Gly Pro Thr Gly Ser Ala Arg Glu Tyr Phe Ala
    210                 215                 220

Pro Asp Asn Gln Leu Pro Leu Val Gln Ser Gly Phe Asn Pro Ser
225                 230                 235                 240

Phe Ile Thr Thr Leu Ser His Glu Lys Gly Ser Ser Asp Thr Ser Glu
                245                 250                 255

Phe Glu Ile Ser Tyr Gly Arg Asn Leu Asp Ile Thr Tyr Ala Thr Leu
            260                 265                 270

Phe Pro Arg Thr Gly Ile Tyr Ala Glu Arg Lys His Asn Ala Phe Val
        275                 280                 285

Asn Arg Asn Phe Val Val Arg Tyr Glu Val Asn Trp Lys Thr His Glu
    290                 295                 300

Ile Lys Val Lys Gly His Asn
305                 310

<210> SEQ ID NO 12
<211> LENGTH: 327
<212> TYPE: PRT
<213> ORGANISM: Staphylococcus aureus

<400> SEQUENCE: 12

Met Lys Met Lys Lys Leu Val Lys Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255
```

```
His Lys Gln Asn Asp Thr Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 13
<211> LENGTH: 327
<212> TYPE: PRT
<213> ORGANISM: Staphylococcus aureus

<400> SEQUENCE: 13

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300
```

```
Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 14
<211> LENGTH: 327
<212> TYPE: PRT
<213> ORGANISM: Staphylococcus aureus

<400> SEQUENCE: 14

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Thr Leu Gly Tyr Ser Tyr
        130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

<210> SEQ ID NO 15
<211> LENGTH: 327
<212> TYPE: PRT
<213> ORGANISM: Staphylococcus aureus

<400> SEQUENCE: 15

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
    290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 16
<211> LENGTH: 327
<212> TYPE: PRT
<213> ORGANISM: Staphylococcus aureus

<400> SEQUENCE: 16

Met Lys Met Lys Lys Leu Val Lys Ser Ser Val Ala Ser Ser Ile Ala

```
1               5                   10                  15
Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Thr Leu Val Leu Lys
65                  70                  75                  80

Ala Ala Gly Asn Ile Asn Ser Gly Tyr Lys Lys Pro Asn Pro Lys Asp
                    85                  90                  95

Tyr Asn Tyr Ser Gln Phe Tyr Trp Gly Gly Lys Tyr Asn Val Ser Val
                100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Gln Thr Leu Gly Tyr Ser Tyr
130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 17
<211> LENGTH: 327
<212> TYPE: PRT
<213> ORGANISM: Staphylococcus aureus

<400> SEQUENCE: 17

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
            35                  40                  45
```

```
Ala Thr Ser Asp Asn Asp Lys Leu Asn Ile Ser Gln Ile Leu Thr Phe
 50                  55                  60

Asn Phe Ile Lys Asp Lys Ser Tyr Asp Lys Asp Thr Leu Val Leu Lys
 65                  70                  75                  80

Ala Ala Gly Asn Ile Asn Ser Gly Tyr Lys Lys Pro Asn Pro Lys Asp
                 85                  90                  95

Tyr Asn Tyr Ser Gln Phe Tyr Trp Gly Gly Lys Tyr Asn Val Ser Val
             100                 105                 110

Ser Ser Glu Ser Asn Asp Ala Val Asn Val Val Asp Tyr Ala Pro Lys
         115                 120                 125

Asn Gln Asn Glu Glu Phe Gln Val Gln Gln Thr Leu Gly Tyr Ser Tyr
130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
        275                 280                 285

Gly Asn Asn Tyr Lys Asn Gln Asn Thr Val Thr Phe Thr Ser Thr Tyr
290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 18
<211> LENGTH: 327
<212> TYPE: PRT
<213> ORGANISM: Staphylococcus aureus

<400> SEQUENCE: 18

Met Lys Met Lys Lys Leu Val Lys Ser Ser Val Ala Ser Ser Ile Ala
 1               5                  10                  15

Leu Leu Leu Leu Ser Asn Thr Val Asp Ala Ala Gln His Ile Thr Pro
                 20                  25                  30

Val Ser Glu Lys Lys Val Asp Asp Lys Ile Thr Leu Tyr Lys Thr Thr
             35                  40                  45

Ala Thr Ser Asp Asn Asp Lys Leu Asn Ile Ser Gln Ile Leu Thr Phe
         50                  55                  60

Asn Phe Ile Lys Asp Lys Ser Tyr Asp Lys Asp Thr Leu Val Leu Lys
 65                  70                  75                  80

Ala Ala Gly Asn Ile Asn Ser Gly Tyr Lys Lys Pro Asn Pro Lys Asp
                 85                  90                  95
```

```
Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Gln Thr Leu Gly Tyr Ser Tyr
            130                 135                 140

Gly Gly Asp Ile Asn Ile Ser Asn Gly Leu Ser Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
            195                 200                 205

Ser Tyr Asp Pro Thr Tyr Gly Asn Glu Leu Phe Leu Gly Gly Arg Gln
            210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
            260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 19
<211> LENGTH: 327
<212> TYPE: PRT
<213> ORGANISM: Staphylococcus aureus

<400> SEQUENCE: 19

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Gln Thr Leu Gly Tyr Ser Tyr
```

```
            130                 135                 140
Gly Gly Asp Ile Asn Ile Ser Asn Gly Leu Ser Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
                195                 200                 205

Ser Tyr Asp Pro Thr Tyr Gly Asn Glu Leu Phe Leu Gly Gly Arg Gln
            210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
                260                 265                 270

Arg Glu Met Asp Arg Tyr Thr Asn Gln Trp Asn Arg Leu His Trp Val
            275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 20
<211> LENGTH: 327
<212> TYPE: PRT
<213> ORGANISM: Staphylococcus aureus

<400> SEQUENCE: 20

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
                100                 105                 110

Ser Ser Glu Ser Asn Asp Ala Val Asn Val Val Asp Tyr Ala Pro Lys
            115                 120                 125

Asn Gln Asn Glu Glu Phe Gln Val Gln Thr Leu Gly Tyr Ser Tyr
            130                 135                 140

Gly Gly Asp Ile Asn Ile Ser Asn Gly Leu Ser Gly Leu Asn Gly
145                 150                 155                 160

Ser Lys Ser Phe Ser Glu Thr Ile Asn Tyr Lys Gln Glu Ser Tyr Arg
                165                 170                 175
```

```
Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
                245                 250                 255

His Lys Gln Asn Asp Thr Lys Lys Ser Lys Ile Lys Val Thr Tyr Gln
                260                 265                 270

Arg Glu Met Asp Arg Tyr Thr Asn Gln Trp Asn Arg Leu His Trp Ile
            275                 280                 285

Gly Asn Asn Tyr Lys Asn Gln Asn Thr Val Thr Phe Thr Ser Thr Tyr
        290                 295                 300

Glu Val Asp Trp Gln Asn His Thr Val Lys Leu Ile Gly Thr Asp Ser
305                 310                 315                 320

Lys Glu Thr Asn Pro Gly Val
                325

<210> SEQ ID NO 21
<211> LENGTH: 327
<212> TYPE: PRT
<213> ORGANISM: Staphylococcus aureus

<400> SEQUENCE: 21

Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
                20                  25                  30

Val Ser Glu Lys Lys Val Asp Asp Lys Ile Thr Leu Tyr Lys Thr Thr
            35                  40                  45

Ala Thr Ser Asp Asn Asp Lys Leu Asn Ile Ser Gln Ile Leu Thr Phe
        50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220
```

```
Ser Ser Ser Asn Ala Gly Gln Asn Phe Leu Pro Thr His Gln Met Pro
225                 230                 235                 240

Leu Leu Ala Arg Gly Asn Phe Asn Pro Glu Phe Ile Ser Val Leu Ser
            245                 250                 255

His Lys Gln Asn Asp Thr Lys Lys Ser Lys Ile Lys Val Thr Tyr Gln
        260                 265                 270

Arg Glu Met Asp Arg Tyr Thr Asn Gln Trp Asn Arg Leu His Trp Ile
    275                 280                 285

Gly Asn Asn Tyr Lys Asn Gln Asn Thr Val Thr Phe Thr Ser Thr Tyr
            290                 295                 300

Glu Val Asp Trp Gln Asn His Thr Val Lys Leu Ile Gly Thr Asp Ser
305                 310                 315                 320

Lys Glu Thr Asn Pro Gly Val
                325
```

<210> SEQ ID NO 22
<211> LENGTH: 327
<212> TYPE: PRT
<213> ORGANISM: Staphylococcus aureus
<220> FEATURE:
<221> NAME/KEY: MISC_FEATURE
<222> LOCATION: (288)..(288)
<223> OTHER INFORMATION: Xaa can be Val or Ile

<400> SEQUENCE: 22

```
Met Lys Met Lys Lys Leu Val Lys Ser Ser Val Ala Ser Ser Ile Ala
1               5                   10                  15

Leu Leu Leu Leu Ser Asn Thr Val Asp Ala Ala Gln His Ile Thr Pro
            20                  25                  30

Val Ser Glu Lys Lys Val Asp Asp Lys Ile Thr Leu Tyr Lys Thr Thr
        35                  40                  45

Ala Thr Ser Asp Asn Asp Lys Leu Asn Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Ala Gly Asn Ile Asn Ser Gly Tyr Lys Lys Pro Asn Pro Lys Asp
                85                  90                  95

Tyr Asn Tyr Ser Gln Phe Tyr Trp Gly Gly Lys Tyr Asn Val Ser Val
            100                 105                 110

Ser Ser Glu Ser Asn Asp Ala Val Asn Val Val Asp Tyr Ala Pro Lys
        115                 120                 125

Asn Gln Asn Glu Glu Phe Gln Val Gln Gln Thr Leu Gly Tyr Ser Tyr
    130                 135                 140

Gly Gly Asp Ile Asn Ile Ser Asn Gly Leu Ser Gly Gly Leu Asn Gly
145                 150                 155                 160

Ser Lys Ser Phe Ser Glu Thr Ile Asn Tyr Lys Gln Glu Ser Tyr Arg
                165                 170                 175

Thr Thr Ile Asp Arg Lys Thr Asn His Lys Ser Ile Gly Trp Gly Val
            180                 185                 190

Glu Ala His Lys Ile Met Asn Asn Gly Trp Gly Pro Tyr Gly Arg Asp
        195                 200                 205

Ser Tyr Asp Pro Thr Tyr Gly Asn Glu Leu Phe Leu Gly Gly Arg Gln
    210                 215                 220

Ser Ser Ser Asn Ala Gly Gln Asn Phe Leu Pro Thr His Gln Met Pro
225                 230                 235                 240
```

-continued

```
Leu Leu Ala Arg Gly Asn Phe Asn Pro Glu Phe Ile Ser Val Leu Ser
            245             250             255

His Lys Gln Asn Asp Thr Lys Lys Ser Lys Ile Lys Val Thr Tyr Gln
            260             265             270

Arg Glu Met Asp Arg Tyr Thr Asn Gln Trp Asn Arg Leu His Trp Xaa
        275             280             285

Gly Asn Asn Tyr Lys Asn Gln Asn Thr Val Thr Phe Thr Ser Thr Tyr
        290             295             300

Glu Val Asp Trp Gln Asn His Thr Val Lys Leu Ile Gly Thr Asp Ser
305             310             315             320

Lys Glu Thr Asn Pro Gly Val
                325
```